(12) United States Patent
Elias et al.

(10) Patent No.: US 10,752,700 B2
(45) Date of Patent: *Aug. 25, 2020

(54) METHODS AND COMPOSITIONS RELATING TO ANTI-CHI3L1 ANTIBODY REAGENTS TO TREAT NONALCOHOLIC STEATOHEPATITIS (NASH), NONALCOHOLIC FATTY LIVER DISEASE (NFALD) OR METABOLIC SYNDROME

(71) Applicant: BROWN UNIVERSITY, Providence, RI (US)

(72) Inventors: Jack A. Elias, Providence, RI (US); Chun Geun Lee, Woodbridge, CT (US); Chuan Hua He, Madison, CT (US); Bing Ma, Branford, CT (US); Suchitra Kamle, Providence, RI (US); Chang-Min Lee, Warwick, RI (US)

(73) Assignee: Brown University, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,128

(22) Filed: Dec. 21, 2018

(65) Prior Publication Data

US 2019/0119405 A1   Apr. 25, 2019

Related U.S. Application Data

(60) Division of application No. 16/124,558, filed on Sep. 7, 2018, now Pat. No. 10,253,111, which is a continuation of application No. PCT/US2018/012494, filed on Jan. 5, 2018.

(60) Provisional application No. 62/442,513, filed on Jan. 5, 2017.

(51) Int. Cl.
| | | |
|---|---|---|
| C07K 16/40 | (2006.01) | |
| A61P 31/04 | (2006.01) | |
| A61P 29/00 | (2006.01) | |
| A61P 35/04 | (2006.01) | |
| A61P 35/00 | (2006.01) | |
| A61P 19/02 | (2006.01) | |
| G01N 33/53 | (2006.01) | |
| A61P 3/04 | (2006.01) | |
| C07K 16/18 | (2006.01) | |
| A61K 39/00 | (2006.01) | |

(52) U.S. Cl.
CPC .............. *C07K 16/40* (2013.01); *A61P 3/04* (2018.01); *A61P 19/02* (2018.01); *A61P 29/00* (2018.01); *A61P 31/04* (2018.01); *A61P 35/00* (2018.01); *A61P 35/04* (2018.01); *C07K 16/18* (2013.01); *G01N 33/53* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,135,884 A | 1/1979 | Shen | |
| 4,305,924 A | 12/1981 | Piasio et al. | |
| 4,444,880 A | 4/1984 | Tom | |
| 4,943,522 A | 7/1990 | Eisinger et al. | |
| 5,585,089 A | 12/1996 | Queen et al. | |
| 5,622,871 A | 4/1997 | May et al. | |
| 5,770,460 A | 6/1998 | Pawlak et al. | |
| 6,187,598 B1 | 2/2001 | May et al. | |
| 6,485,982 B1 | 11/2002 | Charlton | |
| 6,565,808 B2 | 5/2003 | Hudak et al. | |
| 6,809,687 B2 | 10/2004 | Yuanzhu | |
| 6,824,989 B1 | 11/2004 | Eisinger et al. | |
| 6,835,823 B2 | 12/2004 | Le et al. | |
| 7,427,605 B2 | 9/2008 | Davis et al. | |
| 8,172,901 B2 | 5/2012 | Altman et al. | |
| 8,329,660 B2 | 12/2012 | Kuchroo et al. | |
| 8,673,301 B2 | 3/2014 | Bonnichsen et al. | |
| 10,253,111 B2* | 4/2019 | Elias ..................... | G01N 33/53 |
| 2002/0058037 A1 | 5/2002 | Noelle et al. | |
| 2004/0184954 A1 | 9/2004 | Guo et al. | |
| 2007/0190599 A1 | 8/2007 | Nakano et al. | |
| 2011/0009960 A1 | 1/2011 | Altman et al. | |
| 2011/0167602 A1 | 7/2011 | Altman et al. | |
| 2012/0296352 A1 | 11/2012 | Altman et al. | |
| 2018/0092989 A1 | 4/2018 | Lyerly et al. | |

FOREIGN PATENT DOCUMENTS

| | | |
|---|---|---|
| CN | 105092855 A | 11/2015 |
| WO | 1996/023071 A2 | 8/1996 |
| WO | 1997/040068 A1 | 10/1997 |
| WO | 03/063792 A2 | 8/2003 |

OTHER PUBLICATIONS

Canet et al (DMD, 42:586-595, 2014).*
Merchant et al (PNAS, E2987-E2996, 2013).*
Choi et al. "High serum YKL-40 is a poor prognostic marker in patients with advanced non-small cell lung cancer." Acta Oncologica 49(6):861-864 (2010).
Chupp et al., "A chitinase-like protein in the lung and circulation of patients with severe asthma." New England Journal of Medicine 357(20):2016-2027 (2007).
Gussow et al., "Humanization of monoclonal antibodies." Methods in Enzymology 203:99-121 (1991).
Junker et al., "Expression of YKL-40 by peritumoral macrophages in human small cell lung cancer." Lung Cancer 48(2):223-231 (2005).

(Continued)

*Primary Examiner* — Brad Duffy
(74) *Attorney, Agent, or Firm* — Adler Pollock & Sheehan P.C.; Michael Morency

(57) ABSTRACT

Described herein are methods and compositions relating to anti-Chi3L1 antibodies, antibody reagents, and antigen-binding fragments thereof which display superior properties, e.g., high sensitivity, high specificity, high binding affinity, neutralization activity ex vivo and in vivo (e.g., blocks Chi3L1-induced MAPK and AKT signaling). Methods of treatment, e.g., of cancer, obesity, and/or asthma by administering the compounds described herein are also provided.

10 Claims, 20 Drawing Sheets

Specification includes a Sequence Listing.

(56) References Cited

OTHER PUBLICATIONS

Ma et al., "RIG-like Helicase Regulation of Chitinase 3-like 1 Axis and Pulmonary Metastasis." Scientific Reports, 6:26299 (2016).
Ma et al., "Role of Chitinase 3-like-1 and Semaphorin 7a in Pulmonary Melanoma Metastasis." Cancer Research 75(3):487-496 (2015).
Mariuzza et al., "The structural basis of antigen-antibody recognition." Annual review of biophysics and biophysical chemistry 16(1):139-159 (1987).
Steenbakkers et al., "Localization of MHC class II/human cartilage glycoprotein-39 complexes in synovia of rheumatoid arthritis patients using complex-specific monoclonal antibodies." The Journal of Immunology 170(11):5719-5727 (2003).
Thom et al., "Elevated pretreatment serum concentration of YKL-40—An independent prognostic biomarker for poor survival in patients with metastatic non small cell lung cancer." Cancer 116(17):4114-4121 (2010).
Winkler et al., "Changing the antigen binding specificity by single point mutations of an anti-p24 (HIV-1) antibody." The Journal of Immunology 165(8):4505-4514 (2000).
Farrell, et al., "Nonalcoholic Fatty Liver Disease: From Steatosis to Cirrhosis", Hepatology, vol. 43, Feb. 2006, pp. S99-S112.
Lazerow, et al., "Drug-Induced Liver Disease 2004", Curr. Opin. Gastroenterol., vol. 21, No. 3, May 2005, pp. 283-292.
Lorenz, et al., "Steroid and Lipid Conjugates of siRNAs to Enhance Cellular Uptake and Gene Silencing in Liver Cells", Bioorganic & Medicinal Chemistry Letters, vol. 14, Issue 19, Oct. 4, 2004, pp. 4975-4977.
Palekar, et al., "Clinical Model for Distinguishing Nonalcoholic Steatohepatitis from Simple Steatosis in Patients with Nonalcoholic Fatty Liver Disease", Liver Int., vol. 26, No. 2, Mar. 2006, pp. 151-156.

\* cited by examiner

FRG Light Chain IMGTS-CDRs showing KABAT NUMBERS: BETWEEN AMINO ACID SEQUENCE AND NUCLEOTIDE SEQUENCE

```
<----------------------------------FR1-IMGT---------------------------------><-
  D   V   V   M   T   Q   T   P   L   S   L   P   V   S   L   G   D   Q   A   S   I   S   C   R   S   S   Q   S   L   V
  L1  L2  L3  L4  L5  L6  L7  L8  L9  L10 L11 L12 L13 L14 L15 L16 L17 L18 L19 L20 L21 L22 L23 L24 L25 L26 L27 L27A L27B L27C
GATGTTGTGATGACCCAAACTCCACTCTCCCTGCCTGTCAGTCTTGGAGATCAAGCCTCCATCTCTTGCAGATCTAGTCAGAGCCTTGTA  406

<CDR1-IMGT-----------><----------------FR2-IMGT-------------------><-CDR2-IM><
  H   S   N   G   N   T   Y   L   H   W   Y   L   Q   K   P   G   Q   S   P   K   L   L   I   Y   K   V   S   N   R   F
  L27D L27E L27F L28 L29 L30 L31 L32 L33 L34 L35 L36 L37 L38 L39 L40 L41 L42 L43 L44 L45 L46 L47 L48 L49 L50 L51 L52 L53 L54 L55
CACAGTAATGGAAACACCTATTTACATTGGTACCTGCAGAAGCCAGGCCAGTCTCCAAAGCTCCTGATCTACAAAGTTTCCAACCGATTT  496

<-----------------------------------FR3-IMGT-----------------------------------
  S   G   V   P   D   R   F   S   G   S   G   S   G   T   D   F   T   L   K   I   S   R   V   E   A   E   D   L   G   V
  L56 L57 L58 L59 L60 L61 L62 L63 L64 L65 L66 L67 L68 L69 L70 L71 L72 L73 L74 L75 L76 L77 L78 L79 L80 L81 L82 L83 L84 L85
TCTGGGGTCCCAGATCGCTTCAGTGGCAGTGGATCAGGCACAGATTTCACACTCAAGATCAGCAGAGTGGAGGCTGAGGATCTGGGAGTT  586

----------><-----------CDR3-IMGT---------->
  Y   F   C   S   Q   S   T   H   V   T   N   T   F   G   G   G   T   K   L   E   I   K   R   A
  L86 L87 L88 L89 L90 L91 L92 L93 L94 L95 L96 L97 L98 L99 L100 L101 L102 L103 L104 L105 L106 L107 L108 L109
TATTTCTGCTCTCAAAGTACACATGTTACGTGGACGTTCGGTGGAGGCACCAAGCTGGAAATCAAACGGGCT  658
```

FIG. 7

FRG heavy Chain IMGTS-CDRs showing KABAT NUMBERS: BETWEEN AMINO ACID SEQUENCE AND NUCLEOTIDE SEQUENCE

```
<------------------------- FR1 - IMGT -------------------------><--- CDR1 - IM
  Q   I   Q   L   V   Q   S   G   P   E   L   K   K   P   G   E   T   V   K   I   S   C   K   A   S   G   Y   T   F   T
  H1  H2  H3  H4  H5  H6  H7  H8  H9  H10 H11 H12 H13 H14 H15 H16 H17 H18 H19 H20 H21 H22 H23 H24 H25 H26 H27 H28 H29 H30
CAGATCCAGTTGGTGCAGTCTGGACCTGAGCTGAAGAAGCCTGGAGACAGTCAAGATCTCCTGCAAGGCTTCTGGGTATACCTTCACA 349

GT---><------------------------- FR2 - IMGT -------------------------><------- CDR2 - IMGT
  N   Y   G   M   N   W   V   K   Q   A   P   G   K   G   L   K   W   M   G   W   I   N   T   Y   T   G   E   P   T   Y
  H31 H32 H33 H34 H35 H36 H37 H38 H39 H40 H41 H42 H43 H44 H45 H46 H47 H48 H49 H50 H51 H52 H52A H53 H54 H55 H56 H57 H58 H59
AACTATGGAATGAACTGGGTGAAGCAGGCTCCAGGAAAGGGTTTAAAGTGGATGGGATGGATAAATACCTACACTGGAGAGCCAACATAT 439

><------------------------- FR3 - IMGT -------------------------
  A   D   D   F   K   G   R   F   A   F   S   L   E   T   S   A   S   T   A   Y   L   Q   I   N   N   L   R   N   E   D
  H60 H61 H62 H63 H64 H65 H66 H67 H68 H69 H70 H71 H72 H73 H74 H75 H76 H77 H78 H79 H80 H81 H82 H82A H82B H82C H83 H84 H85 H86
GCTGATGACTTCAAGGACCGGTTTGCCTTCTCTTTGGAAACCTCTGCCAGCACTGCCTATTTGCAGATCAACAACCTCAGAAATGAGGAC 529

><------- CDR3 - IMGT --------->
  M   S   T   Y   F   C   A   R   L   G   Y   G   K   F   Y   V   M   D   Y   W   G   Q   G   T   S   V   T   V   S   S
  H87 H88 H89 H90 H91 H92 H93 H94 H95 H96 H97 H98 H99 H100 H100A H100B H100C H100D H101 H102 H103 H104 H105 H106 H107 H108 H109 H110 H111 H112 H113
ATGTCTACATATTTCTGTGCAAGATTGGGATATGGTAAATTCTATGTTATGGACTACTGGGGTCAGGGAACGTCAGTCA 608
```

FIG. 8

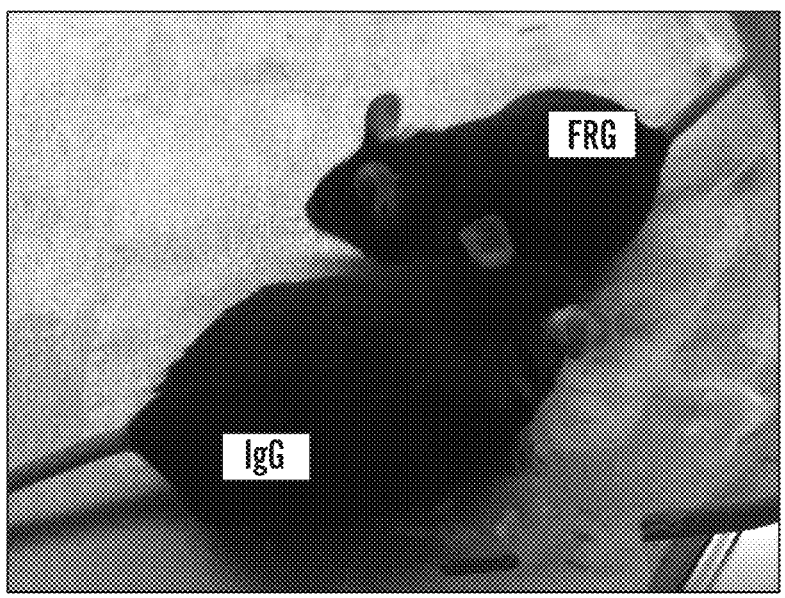
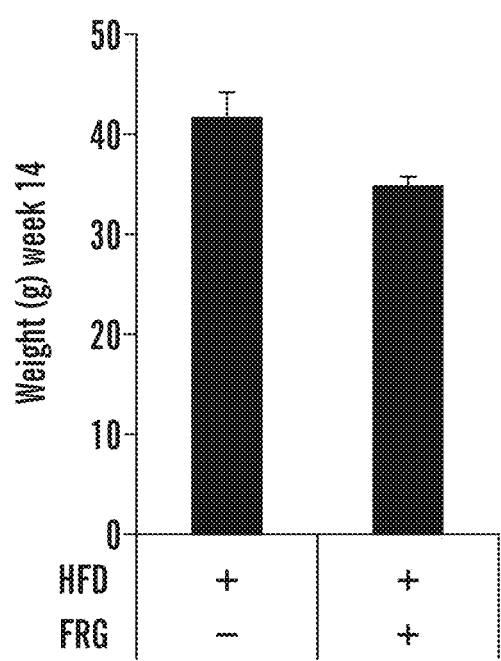
FIG. 11

SEQUENCE LISTING

```
<160> NUMBER OF SEQ ID NOS: 39

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Asn Thr Tyr Thr Gly Glu Pro
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Leu Gly Tyr Gly Lys Phe Tyr Val Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

-continued

```
Gln Ser Leu Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gln Ser Thr His Val Thr Trp Thr
1               5

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggtatacct tcacaaacta tgga                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ataaatacct acactggaga gcca                                          24

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcaagattgg gatatggtaa attctatgtt atggactac                          39

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<210> SEQ ID NO 10
<400> SEQUENCE: 10
cagagccttg tacacagtaa tggaaacacc tat                                    33

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aaagtttcc                                                                9

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctcaaagta cacatgttac gtggacg                                           27

<210> SEQ ID NO 13
<211> LENGTH: 12
<212> TYPE: PRT
<213> ORGANISM: Homo sapiens

<400> SEQUENCE: 13

Phe Arg Gly Gln Glu Asp Ala Ser Pro Asp Arg Phe
1               5                   10

<210> SEQ ID NO 14
<211> LENGTH: 12
<212> TYPE: PRT
<213> ORGANISM: Homo sapiens

<400> SEQUENCE: 14

Arg Gly Ala Thr Val His Arg Ile Leu Gly Gln Gln
1               5                   10

<210> SEQ ID NO 15
<211> LENGTH: 12
<212> TYPE: PRT
<213> ORGANISM: Homo sapiens

<400> SEQUENCE: 15

Ala Ser Ser Glu Thr Gly Val Gly Ala Pro Ile Ser
1               5                   10

<210> SEQ ID NO 16
<211> LENGTH: 12
<212> TYPE: PRT
<213> ORGANISM: Homo sapiens

<400> SEQUENCE: 16

Ile Lys Glu Ala Gln Pro Gly Lys Lys Gln Leu Leu
1               5                   10

<210> SEQ ID NO 17
<211> LENGTH: 12
<212> TYPE: PRT
<213> ORGANISM: Homo sapiens

<400> SEQUENCE: 17

Ser Asn Asp His Ile Asp Thr Trp Glu Trp Asn Asp
1               5                   10

<210> SEQ ID NO 18
<211> LENGTH: 12
<212> TYPE: PRT
<213> ORGANISM: Homo sapiens

<400> SEQUENCE: 18

Tyr Pro Gly Arg Arg Asp Lys Gln His Phe Thr Thr
1               5                   10

<210> SEQ ID NO 19
<211> LENGTH: 12
<212> TYPE: PRT
<213> ORGANISM: Homo sapiens

<400> SEQUENCE: 19

Leu Arg Leu Gly Ala Pro Ala Ser Lys Leu Val Met
1               5                   10

<210> SEQ ID NO 20
<211> LENGTH: 12
<212> TYPE: PRT
<213> ORGANISM: Homo sapiens

<400> SEQUENCE: 20

Pro Gly Ile Pro Gly Arg Phe Thr Lys Glu Ala Gly
1               5                   10

<210> SEQ ID NO 21
<211> LENGTH: 12
<212> TYPE: PRT
<213> ORGANISM: Homo sapiens

<400> SEQUENCE: 21

Gly Ser Gln Arg Phe Ser Lys Ile Ala Ser Asn Thr
1               5                   10

<210> SEQ ID NO 22
<211> LENGTH: 12
<212> TYPE: PRT
<213> ORGANISM: Homo sapiens

<400> SEQUENCE: 22

Gly Lys Val Thr Ile Asp Ser Ser Tyr Asp Ile Ala
1               5                   10

<210> SEQ ID NO 23
<211> LENGTH: 12
<212> TYPE: PRT
<213> ORGANISM: Homo sapiens

<400> SEQUENCE: 23

Gly Met Leu Asn Thr Leu Lys Asn Arg Asn Pro Asn
1               5                   10

<210> SEQ ID NO 24
<211> LENGTH: 12
<212> TYPE: PRT
<213> ORGANISM: Homo sapiens

<400> SEQUENCE: 24

Ser Asn Thr Gln Ser Arg Arg Thr Phe Ile Lys Ser
1               5                   10

<210> SEQ ID NO 25
<211> LENGTH: 383
<212> TYPE: PRT
<213> ORGANISM: Homo sapiens

<400> SEQUENCE: 25

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
                20                  25                  30

Gln Tyr Arg Glu Gly Asp Gly Ser Cys Phe Pro Asp Ala Leu Asp Arg
            35                  40                  45

Phe Leu Cys Thr His Ile Ile Tyr Ser Phe Ala Asn Ile Ser Asn Asp
50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
            115                 120                 125

Thr His Gly Phe Asp Gly Leu Asp Leu Ala Trp Leu Tyr Pro Gly Arg
130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
            195                 200                 205

His Gly Ala Trp Arg Gly Thr Thr Gly His His Ser Pro Leu Phe Arg
210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
            275                 280                 285

Lys Glu Ala Gly Thr Leu Ala Tyr Tyr Glu Ile Cys Asp Phe Leu Arg
290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu

```
                355                 360                 365
Arg Phe Pro Leu Thr Asn Ala Ile Lys Asp Ala Leu Ala Ala Thr
    370                 375                 380

<210> SEQ ID NO 26
<211> LENGTH: 1867
<212> TYPE: DNA
<213> ORGANISM: Homo sapiens

<400> SEQUENCE: 26
cacatagctc agttcccata aagggctgg  tttgccgcgt cggggagtgg agtgggacag      60
gtatataaag gaagtacagg gcctggggaa gaggccctgt ctaggtagct ggcaccagga     120
gccgtgggca agggaagagg ccacaccctg ccctgctctg ctgcagccag aatgggtgtg     180
aaggcgtctc aaacaggctt tgtggtcctg gtgctgctcc agtgctgctc tgcatacaaa     240
ctggtctgct actacaccag ctggtcccag taccgggaag gcgatgggag ctgcttccca     300
gatgcccttg accgcttcct ctgtacccac atcatctaca gctttgccaa tataagcaac     360
gatcacatcg acacctggga gtggaatgat gtgacgctct acggcatgct caacacactc     420
aagaacagga cccccaacct gaagactctc ttgtctgtcg aggatggaa  ctttgggtct     480 caaagatttt ccaagatagc ctccaacacc cagagtcgcc ggactttcat caagtcagta     540
ccgccatttc tgcgcaccca tggctttgat gggctggacc ttgcctggct ctaccctgga     600
cggagagaca acagcatttt accaccccta atcaaggaaa tgaaggccga atttataaag     660
gaagcccagc cagggaaaaa gcagctcctg ctcagcgcag cactgtctgc ggggaaggtc     720
accattgaca gcagctatga cattgccaag atatcccaac cctggatttt cattagcatc     780
atgacctacg attttcatgg agcctggcgt gggaccacag gccatcacag tcccctgttc     840
cgaggtcagg aggatgcaag tcctgacaga ttcagcaaca ctgactatgc tgtggggtac     900
atgttgaggc tgggggctcc tgccagtaag ctggtgatgg catcccac   cttcgggagg     960 agcttcactc tggcttcttc tgagactggt gttggagccc aatctcagg  accgggaatt    1020 ccaggccggt tcaccaagga ggcagggacc cttgcctact atgagatctg tgacttcctc    1080
cgcggagcca cagtccatag aatcctcggc cagcaggtcc cctatgccac caagggcaac    1140
cagtgggtag atacgacga  ccaggaaaag gtcaaaagca aggtgcagta cctgaaggac    1200
aggcagctgg cgggcgccat ggtatgggcc ctggacctgg atgacttcca gggctccttc    1260
tgcggccagg atctgcgctt ccctctcacc aatgccatca aggatgcact cgctgcaacg    1320
tagccctctg ttctgcacac agcacggggg ccaaggatgc cccgtccccc tctggctcca    1380
gctggccggg agcctgatca cctgccctgc tgagtccag  gctgagcctc agtctccctc    1440
ccttggggcc tatgcagagg tccacaacac acagatttga gctcagccct ggtgggcaga    1500
gaggtaggga tggggctgtg gggatagtga ggcatcgcaa tgtaagactc gggattagta    1560
cacacttgtt gattaatgga aatgtttaca gatccccaag cctggcaagg gaatttcttc    1620
aactccctgc cccccagccc tccttatcaa aggacaccat tttggcaagc tctatcacca    1680
aggagccaaa catcctacaa gacacagtga ccatactaat tatccccct  gcaaagccca    1740 gcttgaaacc ttcacttagg aacgtaatcg tgtccctat  cctacttccc cttcctaatt    1800
ccacagctgc tcaataaagt acaagagctt aacagtgaaa aaaaaaaaa  aaaaaaaaa     1860 aaaaaaa                                                              1867

<210> SEQ ID NO 27
```

<211> LENGTH: 383
<212> TYPE: PRT
<213> ORGANISM: Homo sapiens

<400> SEQUENCE: 27

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

```
<210> SEQ ID NO 28
<211> LENGTH: 383
<212> TYPE: PRT
<213> ORGANISM: Homo sapiens

<400> SEQUENCE: 28
```

| | | | | | | | | | | | | | | | |
|---|---|---|---|---|---|---|---|---|---|---|---|---|---|---|---|
| Met | Gly | Val | Lys | Ala | Ser | Gln | Thr | Gly | Phe | Val | Val | Leu | Val | Leu | Leu |
| 1 | | | | 5 | | | | | 10 | | | | | 15 | |
| Gln | Cys | Cys | Ser | Ala | Tyr | Lys | Leu | Val | Cys | Tyr | Tyr | Thr | Ser | Trp | Ser |
| | | | 20 | | | | | 25 | | | | | 30 | | |
| Gln | Tyr | Arg | Glu | Gly | Asp | Gly | Ser | Cys | Phe | Pro | Asp | Ala | Leu | Asp | Arg |
| | | 35 | | | | | 40 | | | | | 45 | | | |
| Phe | Leu | Cys | Thr | His | Ile | Ile | Tyr | Ser | Phe | Ala | Asn | Ile | Ser | Asn | Asp |
| 50 | | | | | 55 | | | | | 60 | | | | | |
| His | Ile | Asp | Thr | Trp | Glu | Trp | Asn | Asp | Val | Thr | Leu | Tyr | Gly | Met | Leu |
| 65 | | | | 70 | | | | | 75 | | | | | 80 | |
| Asn | Thr | Leu | Lys | Asn | Arg | Asn | Pro | Asn | Leu | Lys | Thr | Leu | Leu | Ser | Val |
| | | | 85 | | | | | 90 | | | | | 95 | | |
| Gly | Gly | Trp | Asn | Phe | Gly | Ser | Gln | Arg | Phe | Ser | Lys | Ile | Ala | Ser | Asn |
| | | | 100 | | | | | 105 | | | | | 110 | | |
| Thr | Gln | Ser | Arg | Arg | Thr | Phe | Ile | Lys | Ser | Val | Pro | Pro | Phe | Leu | Arg |
| | | | 115 | | | | | 120 | | | | | 125 | | |
| Thr | His | Gly | Phe | Asp | Gly | Leu | Asp | Leu | Ala | Trp | Leu | Tyr | Pro | Gly | Arg |
| | | 130 | | | | | 135 | | | | | 140 | | | |
| Arg | Asp | Lys | Gln | His | Phe | Thr | Thr | Leu | Ile | Lys | Glu | Met | Lys | Ala | Glu |
| 145 | | | | | 150 | | | | | 155 | | | | | 160 |
| Phe | Ile | Lys | Glu | Ala | Gln | Pro | Gly | Lys | Lys | Gln | Leu | Leu | Leu | Ser | Ala |
| | | | | 165 | | | | | 170 | | | | | 175 | |
| Ala | Leu | Ser | Ala | Gly | Lys | Val | Thr | Ile | Asp | Ser | Ser | Tyr | Asp | Ile | Ala |
| | | | 180 | | | | | 185 | | | | | 190 | | |
| Lys | Ile | Ser | Gln | His | Leu | Asp | Phe | Ile | Ser | Ile | Met | Thr | Tyr | Asp | Phe |
| | | 195 | | | | | 200 | | | | | 205 | | | |
| His | Gly | Ala | Trp | Arg | Gly | Thr | Thr | Gly | His | His | Ser | Pro | Leu | Phe | Arg |
| | | 210 | | | | | 215 | | | | | 220 | | | |
| Gly | Gln | Glu | Asp | Ala | Ser | Pro | Asp | Arg | Phe | Ser | Asn | Thr | Asp | Tyr | Ala |
| 225 | | | | | 230 | | | | | 235 | | | | | 240 |
| Val | Gly | Tyr | Met | Leu | Arg | Leu | Gly | Ala | Pro | Ala | Ser | Lys | Leu | Val | Met |
| | | | | 245 | | | | | 250 | | | | | 255 | |
| Gly | Ile | Pro | Thr | Phe | Gly | Arg | Ser | Phe | Thr | Leu | Ala | Ser | Ser | Glu | Thr |
| | | | 260 | | | | | 265 | | | | | 270 | | |
| Gly | Val | Gly | Ala | Pro | Ile | Ser | Gly | Pro | Gly | Ile | Pro | Gly | Arg | Phe | Thr |
| | | 275 | | | | | 280 | | | | | 285 | | | |
| Lys | Glu | Ala | Gly | Thr | Leu | Ala | Tyr | Tyr | Glu | Ile | Cys | Asp | Phe | Leu | Arg |
| | 290 | | | | | 295 | | | | | 300 | | | | |
| Gly | Ala | Thr | Val | His | Arg | Ile | Leu | Gly | Gln | Gln | Val | Pro | Tyr | Ala | Thr |
| 305 | | | | | 310 | | | | | 315 | | | | | 320 |
| Lys | Gly | Asn | Gln | Trp | Val | Gly | Tyr | Asp | Asp | Gln | Glu | Ser | Val | Lys | Ser |
| | | | | 325 | | | | | 330 | | | | | 335 | |
| Lys | Val | Gln | Tyr | Leu | Lys | Asp | Arg | Gln | Leu | Ala | Gly | Ala | Met | Val | Trp |
| | | | 340 | | | | | 345 | | | | | 350 | | |
| Ala | Leu | Asp | Leu | Asp | Asp | Phe | Gln | Gly | Ser | Phe | Cys | Gly | Gln | Asp | Leu |
| | | | 355 | | | | | 360 | | | | | 365 | | |
| Arg | Phe | Pro | Leu | Thr | Asn | Ala | Ile | Lys | Asp | Ala | Leu | Ala | Ala | Thr | |
| | 370 | | | | | 375 | | | | | 380 | | | | |

```
<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Gly Gly Ser
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5

<210> SEQ ID NO 31
<211> LENGTH: 1925
<212> TYPE: DNA
<213> ORGANISM: Homo sapiens

<400> SEQUENCE: 31
agtggagtgg gacaggtata taaaggaagt acagggcctg gggaagaggc cctgtctagg      60
tagctggcac caggagccgt gggcaaggga agaggccaca ccctgccctg ctctgctgca     120
gccagaatgg gtgtgaaggc gtctcaaaca ggctttgtgg tcctggtgct gctccagtgc     180
tgctctgcat acaaactggt ctgctactac accagctggt cccagtaccg ggaaggcgat     240
gggagctgct tcccagatgc ccttgaccgc ttcctctgta cccacatcat ctacagcttt     300
gccaatataa gcaacgatca catcgacacc tgggagtgga tgatgtgac gctctacggc      360 atgctcaaca cactcaagaa caggaacccc aacctgaaga ctctcttgtc tgtcggagga     420
tggaactttg gtctcaaag atttttccaag atagcctcca cacccagag tcgccggact      480 ttcatcaagt cagtaccgcc attcctgcgc acccatggct tgatgggct ggaccttgcc      540 tggctctacc ctggacggag agacaaacag cattttacca ccctaatcaa ggaaatgaag     600
gccgaattta taaggaagc ccagccaggg aaaaagcagc tcctgctcag cgcagcactg      660
tctgcgggga aggtcaccat tgacagcagc tatgacattg ccaagatatc ccaacacctg     720
gatttcatta gcatcatgac ctacgatttt catggagcct ggcgtgggga cacaggccat     780
cacagtcccc tgttccgagg tcaggaggat gcaagtcctg acagattcag caacactgac     840
tatgctgtgg ggtacatgtt gaggctgggg gctcctgcca gtaagctggt gatgggcatc     900
cccaccttcg ggaggagctt cactctggct tcttctgaga ctggtgttgg agccccaatc     960
tcaggaccgg gaattccagg ccggttcacc aaggaggcag ggaccccttgc ctactatgag    1020 atctgtgact tcctccgcgg agccacagtc catagaaccc tcggccagca ggtcccctat    1080
gccaccaagg gcaaccagtg ggtaggatac gacgaccagg aaagcgtcaa aagcaaggtg    1140
cagtacctga aggataggca gctggcaggc gccatggtat gggccctgga cctggatgac    1200
ttccagggct ccttctgcgg ccaggatctg cgcttccctc tcaccaatgc catcaaggat    1260
gcactcgctg caacgtagcc ctctgttctg cacacagcac gggggccaag gatgccccgt    1320
```

```
cccctctgg ctccagctgg ccgggagcct gatcacctgc cctgctgagt cccaggctga    1380
gcctcagtct ccctcccttg gggcctatgc agaggtccac aacacacaga tttgagctca    1440
gccctggtgg gcagagaggt agggatgggg ctgtggggat agtgaggcat cgcaatgtaa    1500
gactcgggat tagtacacac ttgttgatga ttaatggaaa tgtttacaga tccccaagcc    1560
tggcaaggga atttcttcaa ctccctgccc cctagccctc cttatcaaag gacaccattt    1620
tggcaagctc tatcaccaag gagccaaaca tcctacaaga cacagtgacc atactaatta    1680
taccccctgc aaagccagct tgaaaccttc acttaggaac gtaatcgtgt ccctatcct     1740 acttccccttt cctaattcca cagctgctca ataaagtaca agagtttaac agtgtgttgg    1800
cgctttgctt tggtctatct ttgagcgccc actagaccca ctggactcac ctcccccatc    1860
tcttctgggt tccttcctct gagccttggg acccctgagc ttgcagagat gaaggccgcc    1920
atgtt                                                                1925
```

<210> SEQ ID NO 32
<211> LENGTH: 114
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 32

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Thr Trp Thr Phe Gly Gly Gly Thr Lys Leu Glu Ile Lys
            100                 105                 110

Arg Ala

<210> SEQ ID NO 33
<211> LENGTH: 342
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 33

```
gatgttgtga tgacccaaac tccactctcc ctgcctgtca gtcttggaga tcaagcctcc    60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttacg    300
tggacgttcg gtggaggcac caagctggaa atcaaacggg ct                      342
```

<210> SEQ ID NO 34
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 35
<211> LENGTH: 349
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaatacct acactggaga gccaacatat     180
gctgatgact caagggacg gttttgccttc tctttggaaa cctctgccag cactgcctat    240
ttgcagatca caacctcag aaatgaggac atgtctacat atttctgtgc aagattggga      300
tatggtaaat tctatgttat ggactactgg ggtcaggga cgtcagtca                  349

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
            50                  55                  60

Lys Gly Arg Phe Ala Phe Ser Leu Glu Thr Ser Ala Ser Thr Ala Tyr
 65                  70                  75                  80

Leu Gln Ile Asn Asn Leu Arg Asn Glu Asp Met Ser Thr Tyr Phe Cys
                 85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
            115                 120

<210> SEQ ID NO 37
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaatacct acactggaga gccaacatat     180
gctgatgact caagggacg gtttgccttc tctttggaaa cctctgccag cactgcctat      240
ttgcagatca caacctcag aaatgaggac atgtctacat atttctgtgc aagattggga     300
tatggtaaat tctatgttat ggactactgg ggtcaggaa cgtcagtcac cgtctcctca     360

<210> SEQ ID NO 38
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Thr Trp Thr Phe Gly Gly Gly Thr Lys Leu Glu Ile Lys
            100                 105                 110

<210> SEQ ID NO 39
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 39
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttacg     300
tggacgttcg gtggaggcac caagctggaa atcaaa                               336
```

METHODS AND COMPOSITIONS RELATING TO ANTI-CHI3L1 ANTIBODY REAGENTS TO TREAT NONALCOHOLIC STEATOHEPATITIS (NASH), NONALCOHOLIC FATTY LIVER DISEASE (NFALD) OR METABOLIC SYNDROME

CROSS-REFERENCE TO RELATED APPLICATIONS

This application is a divisional of co-pending U.S. application Ser. No. 16/124,558 filed Sep. 7, 2018, which claims benefit under 35 U.S.C. § 365(c) and 35 U.S.C. § 120 of International Application No. PCT/US18/012494 filed Jan. 5, 2018, which designates the U.S. and which claims benefit under 35 U.S.C. § 119(e) of U.S. Provisional Application No. 62/442,513 filed Jan. 5, 2017, the contents of which are incorporated herein by reference in their entireties.

GOVERNMENT SUPPORT

This invention was made with government support under Grant Nos. UH2 HL 123876 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 10, 2018, is named 2018-01-05_Seq_Listing_058040-088262-PCT.txt and is 27,672 bytes in size.

TECHNICAL FIELD

The technology described herein relates to antibodies and antibody-based reagents that are specific for CHI3L1 and methods of using those compositions, e.g., to treat cancer or asthma.

BACKGROUND

The chitinase-like protein called chitinase 3-like-1 (Chi3l1; also called Chil1 in mice and YKL-40 in man) has been implicated in asthma and cancer, e.g., lung cancer. It has been demonstrated that the levels of circulating Chi3l1 are increased in human asthma where they correlate with disease severity. The levels of circulating YKL-40 are increased in many malignancies including cancers of the prostate, colon, rectum, ovary, kidney, breast, glioblastomas and malignant melanoma. In these diseases, the levels of YKL-40 frequently correlate directly with disease progression and inversely with disease-free interval and survival.

SUMMARY

Described herein are the development and characterization of anti-CHI3L1 antibodies demonstrated to have high specificity and the ability to block CHI3L1 activity. These antibodies are further demonstrated to have therapeutic activity in asthma and cancer models.

In one aspect of any of the embodiments, described herein is an antibody, antibody reagent, antigen-binding fragment thereof, or chimaeric antigen receptor (CAR), that specifically binds an CHI3L1 polypeptide, said antibody reagent, antigen-binding portion thereof, or CAR comprising at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or a conservative substitution variant of one or more of (a)-(f).

In some embodiments of any of the aspects, the antibody, antibody reagent, antigen-binding portion thereof, or CAR comprises heavy chain CDRs having the amino acid sequences of SEQ ID NOs: 1-3 or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 4-6 or a conservative substitution variant of such amino acid sequence. In some embodiments of any of the aspects, the antibody, antibody reagent, antigen-binding portion thereof, or CAR comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

In one aspect of any of the embodiments, described herein is an antibody, antibody reagent, antigen-binding portion thereof, or CAR that specifically binds an CHI3L1 polypeptide, and can compete for binding of CHI3L1 with an antibody comprising light chain CDRs having the amino acid sequences of SEQ ID NOs: 4-6 and heavy chain CDRs having the amino acid sequences of SEQ ID NOs: 1-3.

In some embodiments of any of the aspects, the antibody, antibody reagent or antigen-binding fragment thereof binds to the epitope of SEQ ID NO: 13.

In one aspect of any of the embodiments, described herein is an antibody, antibody reagent, antigen-binding portion thereof, or CAR of claim 5 or 6, wherein the antibody, antibody reagent or antigen-binding fragment thereof binds an CHI3L1 polypeptide at an eptitope selected from SEQ ID NOs: 13-24.

In some embodiments of any of the aspects, the antibody, antibody reagent, antigen-binding portion thereof, or CAR further comprises a conservative substitution in a sequence not comprised by a CDR. In some embodiments of any of the aspects, the antibody, antibody reagent, antigen-binding portion thereof, or CAR is fully human or fully humanized. In some embodiments of any of the aspects, the antibody, antibody reagent, antigen-binding portion thereof, or CAR is fully humanized except for the CDR sequences.

In some embodiments of any of the aspects, the reagent or fragment is selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

In one aspect of any of the embodiments of any of the aspects, described herein is a composition comprising the antibody, antibody reagent, antigen-binding portion thereof, or CAR as described herein, and a chemotherapeutic agent. In some embodiments of any of the aspects, wherein the antibody, antibody reagent, or antigen-binding portion thereof is conjugated to the chemotherapeutic agent.

In one aspect of any of the embodiments, described herein is a nucleic acid sequence encoding the antibody, antibody reagent, antigen-binding fragment thereof, or CAR as described herein, wherein at least one CDR is encoded by a nucleic acid sequence selected from SEQ ID NOs: 7-12.

In one aspect of any of the embodiments, described herein is a cell comprising the antibody, antibody reagent, antigen-binding fragment thereof, CAR or the nucleic acid sequence as described herein.

In one aspect of any of the embodiments, described herein is a pharmaceutical composition comprising the antibody, antibody reagent, antigen-binding fragment thereof, CAR, composition, or cell as described herein and a pharmaceutically acceptable carrier.

In one aspect of any of the embodiments, described herein is a solid support comprising the antibody, antibody reagent, antigen-binding fragment thereof, or CAR as described herein. In some embodiments of any of the aspects, the antibody, antibody reagent, antigen-binding fragment thereof, or CAR is detectably labeled. In some embodiments of any of the aspects, the solid support comprises a particle, a bead, a polymer, or a substrate.

In one aspect of any of the embodiments, described herein is a kit for the detection of CHI3L1 polypeptide in a sample, the kit comprising at least a first antibody, antibody reagent, antigen-binding fragment thereof, or CAR as described herein, immobilized on a solid support and comprising a detectable label.

In one aspect of any of the embodiments, described herein is a molecular complex comprising at least one antibody, antibody reagent, antigen-binding fragment thereof, or CAR as described herein bound to an CHI3L1 polypeptide.

In one aspect of any of the embodiments, described herein is a method of treating cancer in a subject in need thereof, the method comprising administering the antibody, antibody reagent, antigen-binding fragment thereof, CAR, composition, or cell as described herein to the subject. In some embodiments of any of the aspects, the cancer is primary cancer. In some embodiments of any of the aspects, the cancer is malignant cancer. In some embodiments of any of the aspects, the cancer is selected from the group consisting of: prostate cancer, colon cancer, rectal cancer, ovarian cancer, kidney cancer, breast cancer, glioblastoma, melanoma, malignant melanoma, and lung cancer.

In one aspect of any of the embodiments, described herein is a method of treating asthma in a subject in need thereof, the method comprising administering the antibody, antibody reagent, antigen-binding fragment thereof, CAR, composition, or cell as described herein to the subject.

In one aspect of any of the embodiments, described herein is a method of treating obesity and/or preventing weight gain in a subject in need thereof, the method comprising administering the antibody, antibody reagent, antigen-binding fragment thereof, CAR, composition, or cell as described herein to the subject. In one aspect of any of the embodiments, described herein is a method of promoting weight loss in a subject in need thereof, the method comprising administering the antibody, antibody reagent, antigen-binding fragment thereof, CAR, composition, or cell as described herein to the subject.

In some embodiments of any of the aspects, the subject is a subject determined to have an elevated level of CHI3L1. In some embodiments of any of the aspects, the CHI3L1 is circulating CHI3L1.

BRIEF DESCRIPTION OF THE DRAWINGS

FIG. 1A demonstrates mAb analysis in Coomassie staining, Western blot and Isotyping. FIG. 1B depicts FRG detection of Chi3l1 in non-denaturing and denaturing conditions. FIG. 1C depicts Sensitivity and specificity of FRG against recombinant (r) human and mouse Chi3l1 detected by Western blot. FIG. 1D depicts FRG affinity and dose response curve evaluated by ELISA.

FIG. 2A depicts effects on peritoneal macrophages*. FIG. 2B depicts effects on peritoneal macrophages—dose response*. * Thp1 cells, U937 cells, and AMJ2-C11 (mouse alveolar macrophages cell line) showed similar pattern of inhibition and dose responses on Chi3l1-stimulated Erk and Akt activation.

FIG. 5A depicts representative lungs from the KRAS/p53 mutant mice treated with control (Ctrl) igG or FRG mAb. FIG. 5B depicts a representative histology of the lungs illustrated in FIG. 5A.

FIG. 7 depicts the light chain CDR sequences of the FRG antibody described herein. Figure discloses SEQ ID NOS 32-33, respectively, in order of appearance.

FIG. 8 depicts the heavy chain CDR sequences of the FRG antibody described herein. Figure discloses SEQ ID NOS 34-35, respectively, in order of appearance.

FIG. 11 depicts an image and a graph of body weight changes at 14th week HFD with & without FRG

DETAILED DESCRIPTION

Figure 1A:
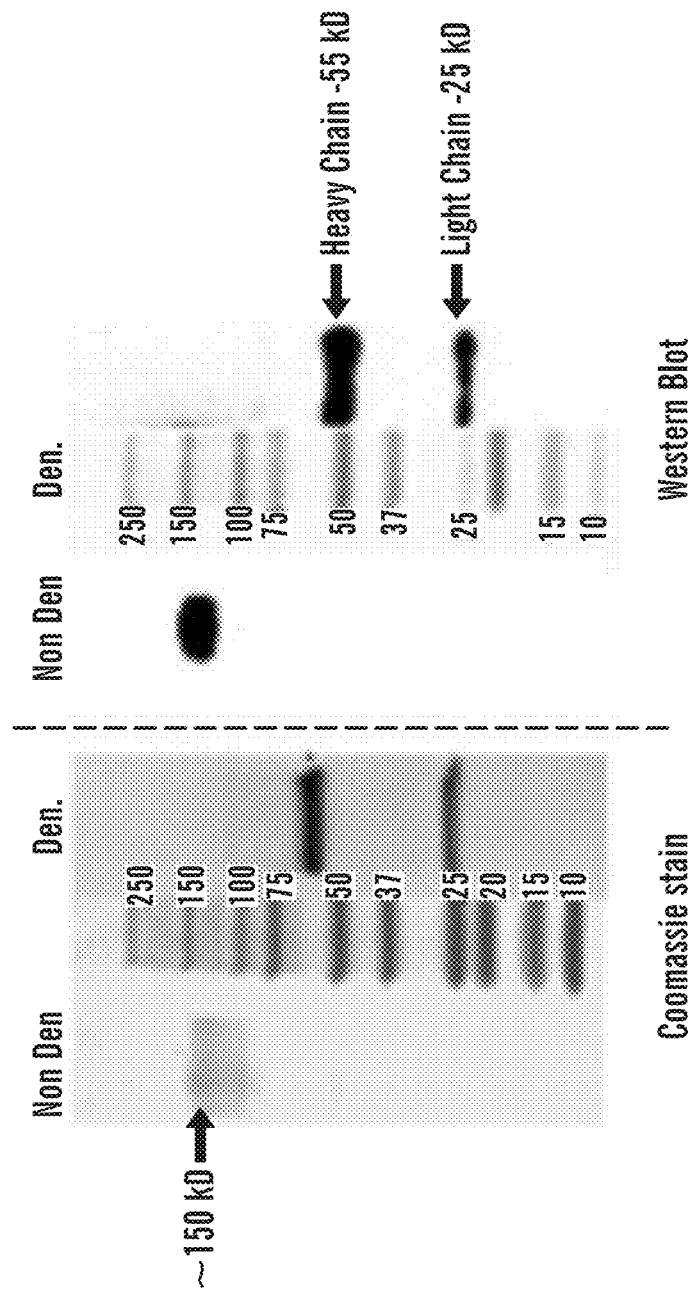
FIGS. 1A-1D depict the characterization of the FRG monoclonal antibody (mAb).
Figure 1A:
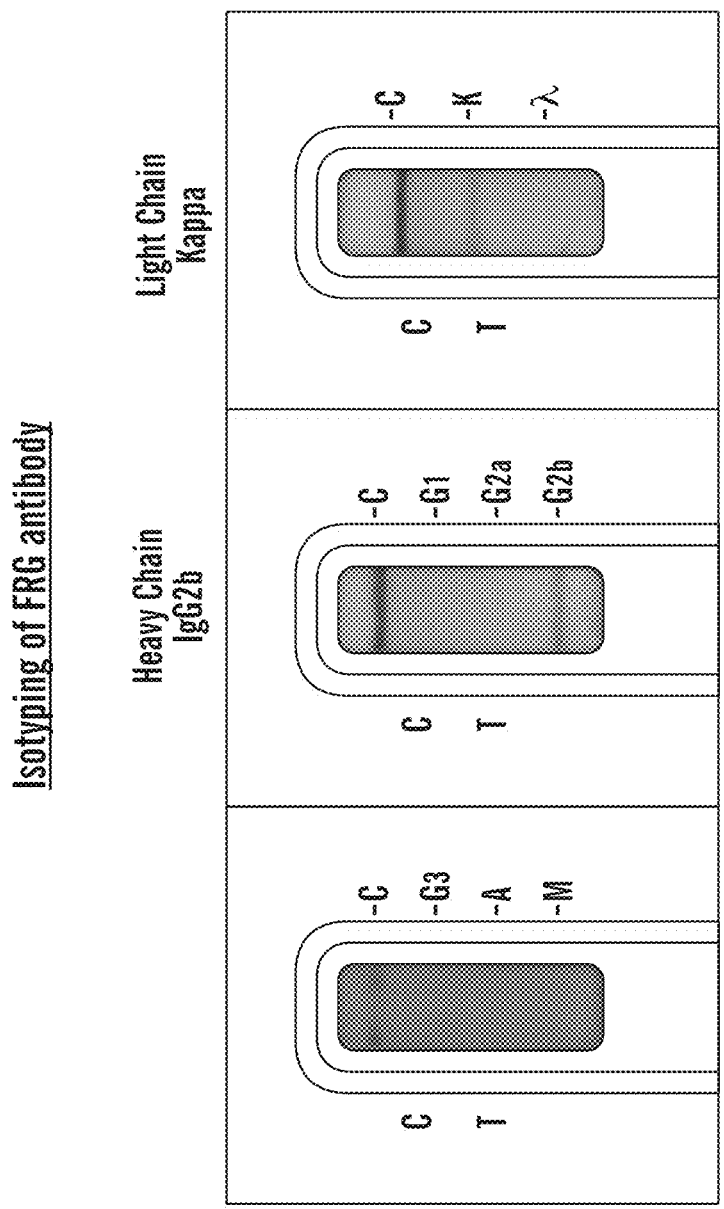
Figure 1B:
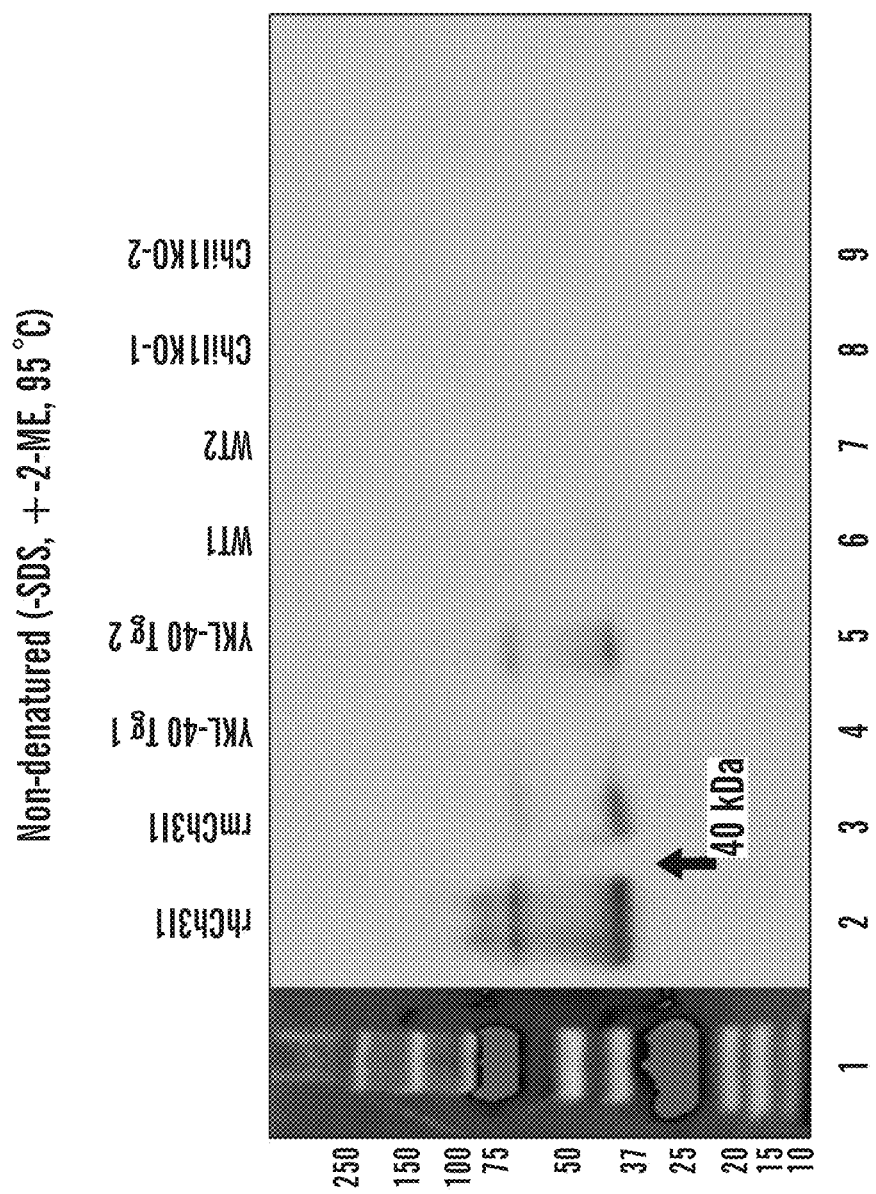
Figure 1B:
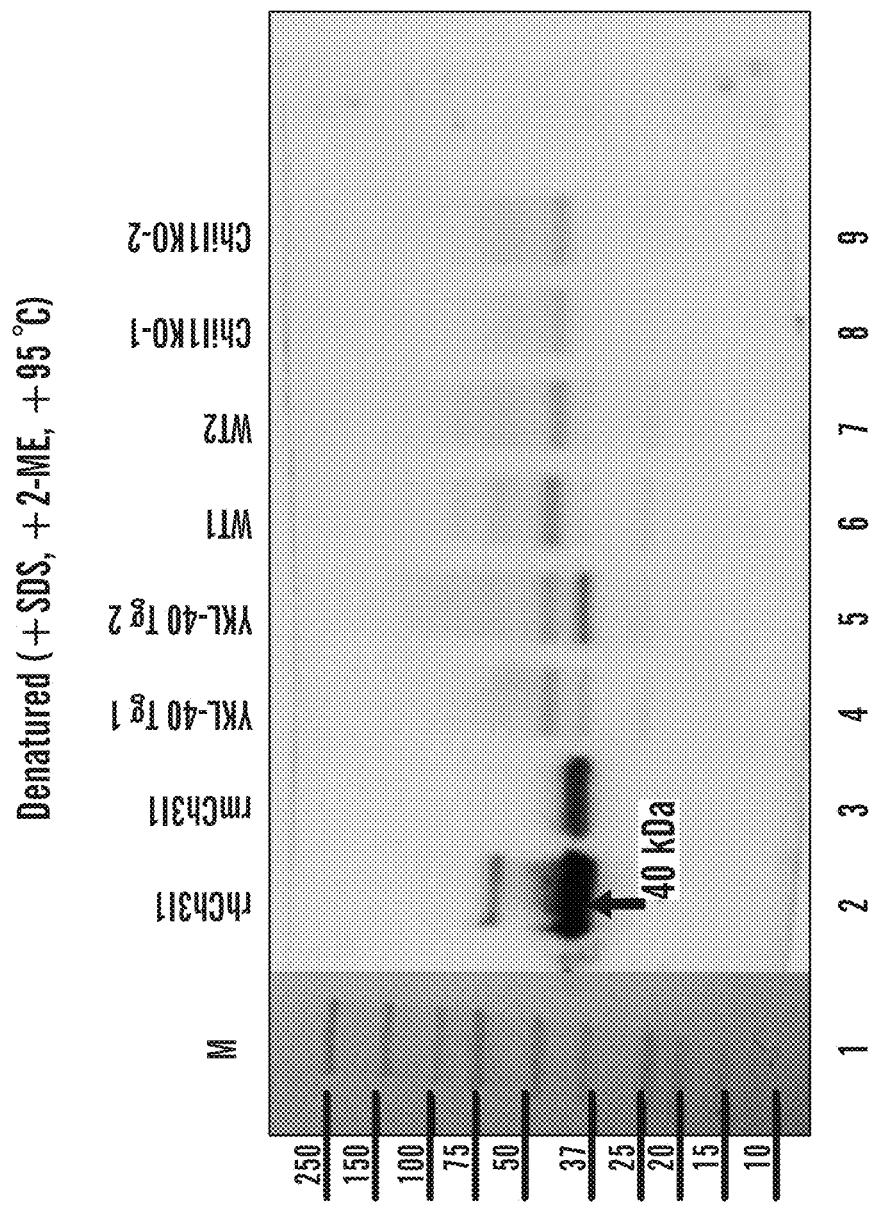
Figure 1C:
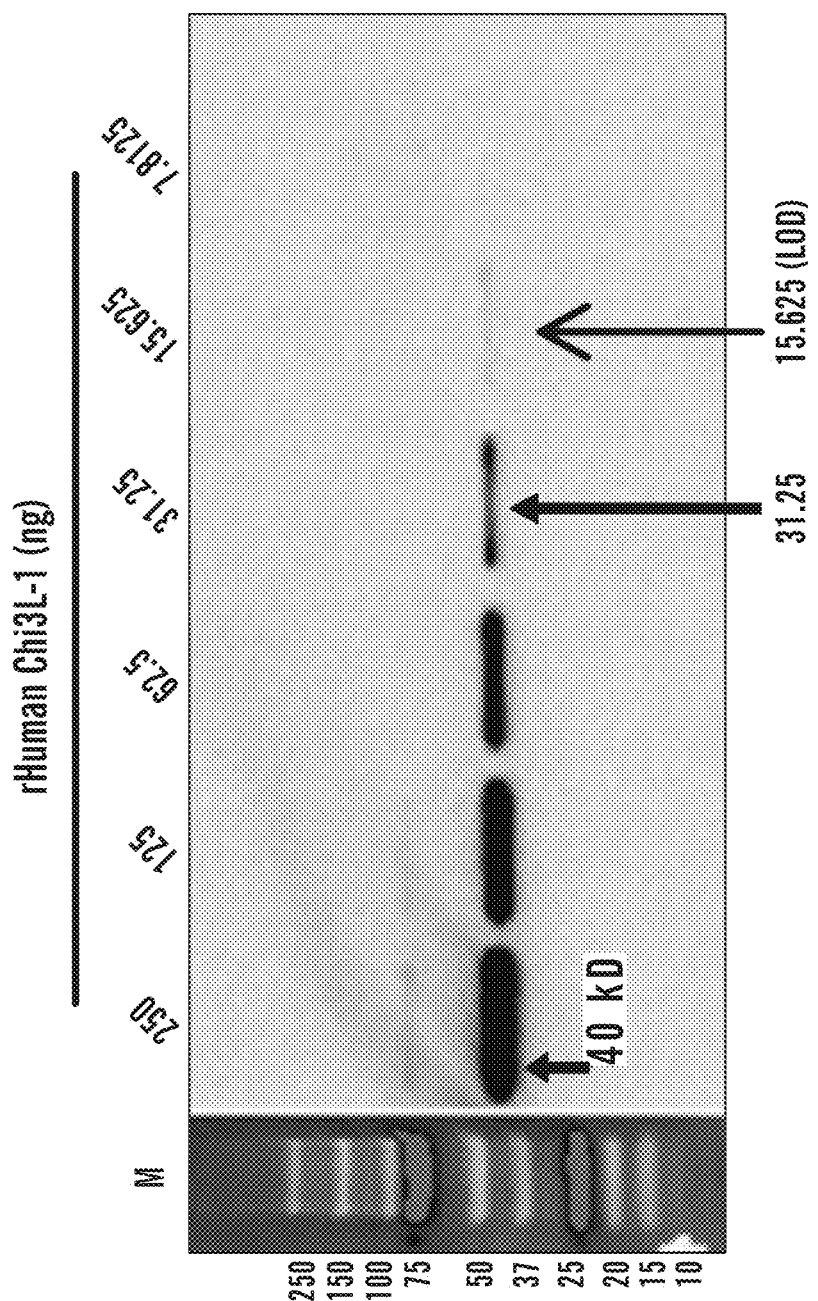
Figure 1C:
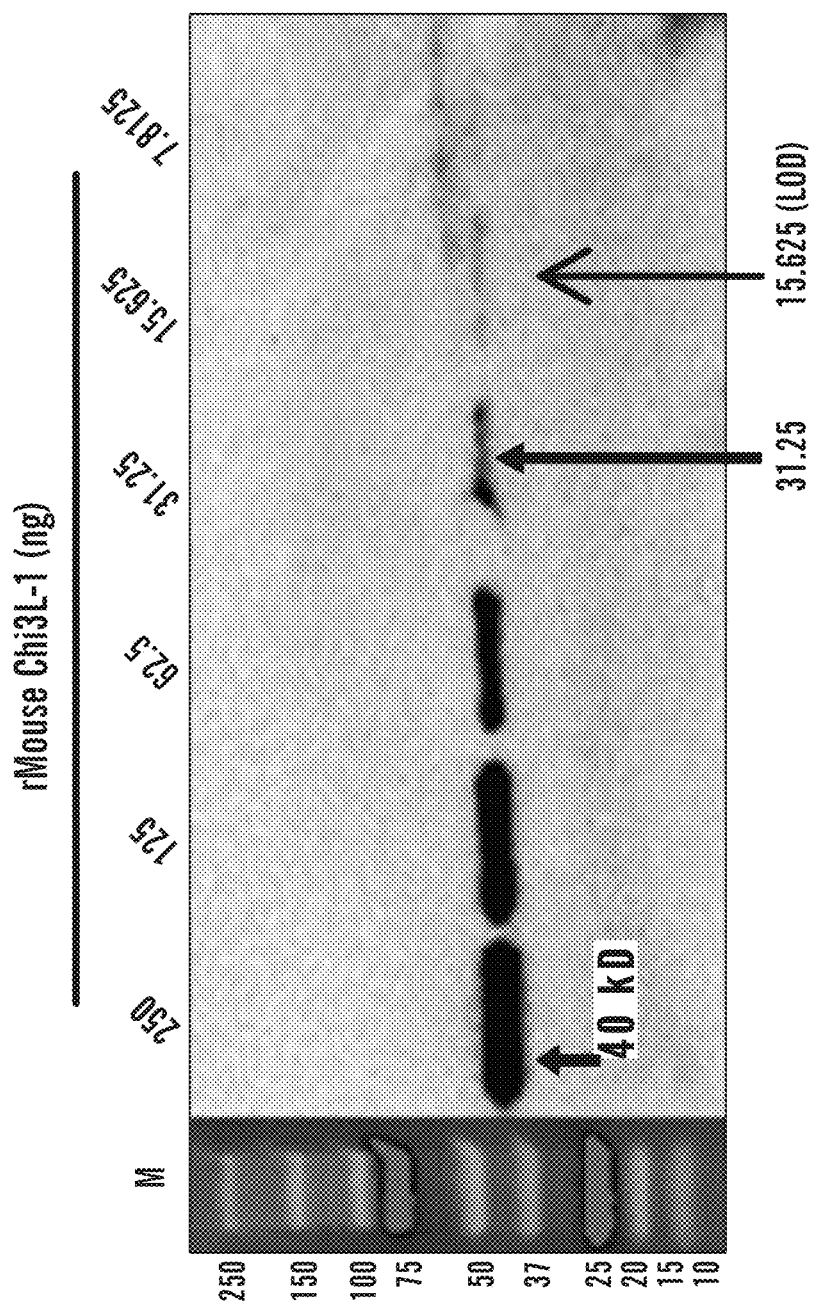
Figure 1D:
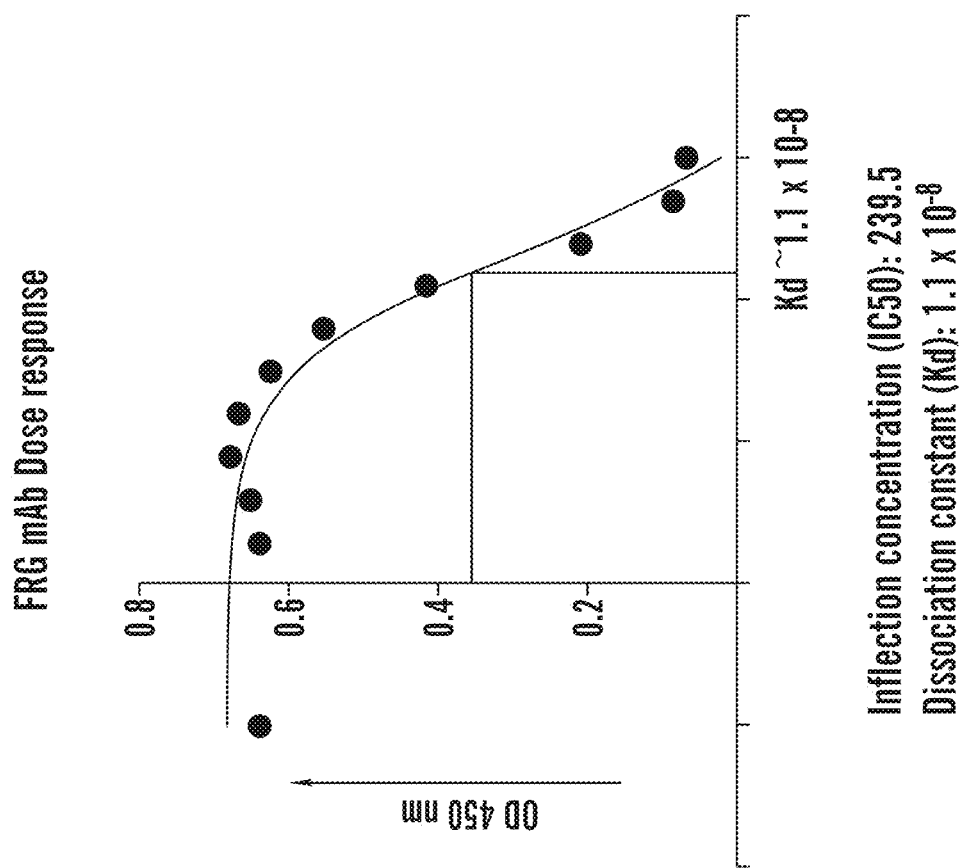
Figure 1D:
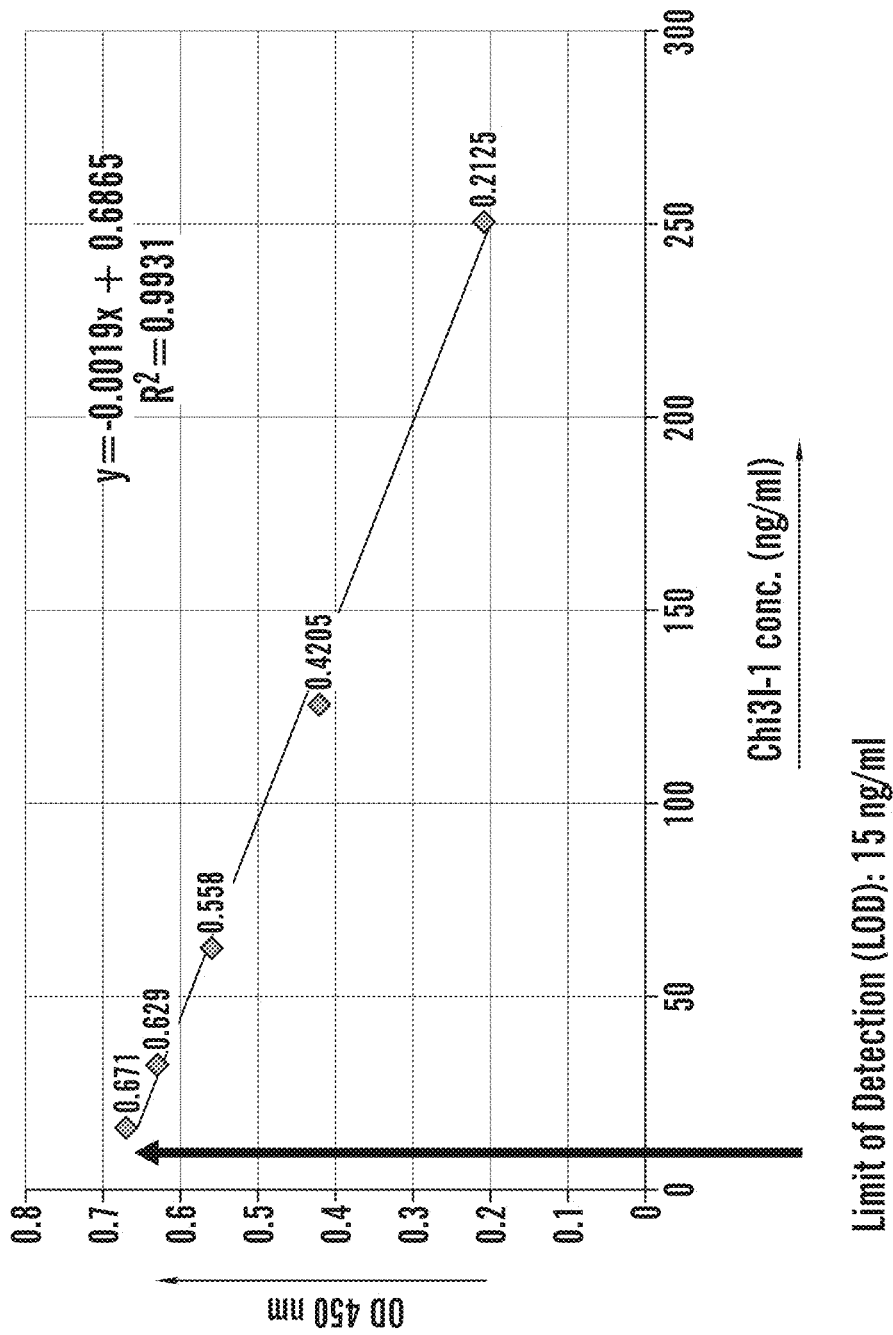

Described herein are antibodies, antibody reagents, antigen-binding fragments thereof, or chimaeric antigen receptors (CARs) that specifically bind a CHI3L1 polypeptide. Such antibodies, antigen binding portions thereof, etc., can permit, e.g., the diagnosis, prognosis, and/or treatment of cancer or asthma. In some embodiments, the technology described herein relates to chimeric antigen receptors (CARs) and CAR-T therapy for cancer or asthma. In some embodiments, the technology described herein relates to monoclonal antibody therapy for cancer or asthma. In some embodiments, the technology described herein relates to antibody-drug conjugates for the treatment of cancer or cancer.

Described herein are methods and compositions relating to anti-Chi3L1 antibodies, antibody reagents, and antigen-binding fragments thereof which display superior properties, e.g., high sensitivity, high specificity, high binding affinity, neutralization activity ex vivo and in vivo (e.g., blocks Chi3L1-induced MAPK and AKT signaling). Methods of treatment, e.g., of treating cancer, obesity, and/or asthma by administering the compounds described herein are also provided.

As used herein, "CHI3L1," "chitinase-3-like protein 1," or "YKL-40" refers to a ~40 kDa glycoprotein secreted by at least macrophages, chondrocytes, neutrophils, synovial cells, and some cancer cells. CHI3L1 does not have chitinase activity, is a Th2 promoting cytokine, has been linked to the AKT anti-apoptotic signaling pathway and induces the migration of astrocytes. The sequences of CHI3L1 expression products are known for a number of species, e.g., human CHI3L1 (NCBI Gene ID No: 1116) mRNA (SEQ ID NO: 31; NCBI Ref Seq: NM_001276.1 and SEQ ID NO: 26; NCBI Ref Seq: NM_001276.2) and polypeptide (SEQ ID NO: 27; NCBI Ref Seq: NP_001267.1 and SEQ ID NO: 28; NCBI Ref Seq: NP_001267.2).

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs. The CDR's identified herein, e.g., SEQ ID NOs 1-6 are identified by the Kabat system (see, e.g. FIGS. 7 and 8).

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only VL domains have also been shown to specifically bind to target eptiopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 29), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cystein residue, a marker peptide and a C-terminal polyhistidinyl, e.g., hexahistidinyl tag ('hexahistidinyl tag' disclosed as SEQ ID NO: 30) in order to produce bivalent and biotinylated scFv molecules.

In some embodiments, the antibody, antibody reagent, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide. In some embodiments, the CAR comprises an extracellular domain that binds CHI3L1, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. In some embodiments, it is possible to make one or more conservative amino acid substitutions of CDR residues without appreciably affecting the binding affinity of the resulting humanized immunoglobulin or human antibody variant. In some embodiments, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARs described herein).

In some embodiments, the antibody reagents (e.g., antibodies or CARs) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments, the antibody, antibody reagent, antigen-binding portion thereof, and/or CAR is an isolated polypeptide. In some embodiments, the antibody, antibody reagent, antigen-binding portion thereof, and/or CAR is a purified polypeptide. In some embodiments, the antibody, antibody reagent, antigen-binding portion thereof, and/or CAR is an engineered polypeptide.

In one aspect of any of the embodiments, described herein is an antibody, antigen-binding fragment thereof, antigen reagent or chimaeric antigen receptor (CAR), that specifically binds a CHI3L1 polypeptide. In some embodiments of any of the aspects, the antibody, antigen-binding fragment thereof, antigen reagent or CAR comprises at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or a conservative substitution variant of one or more of (a)-(f). In some embodiments of any of the aspects, the antibody, antigen-binding fragment thereof, antigen reagent or CAR comprises at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3. In some embodiments of any of the aspects, the antibody, antibody reagent, antigen-binding portion thereof, or CAR that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

In some embodiments of any of the aspects, the antibody, antigen-binding fragment thereof, antigen reagent or CAR comprises heavy chain CDRs having the amino acid sequences of SEQ ID NOs: 1-3. In some embodiments of any of the aspects, the antibody, antigen-binding fragment thereof, antigen reagent or CAR comprises heavy chain CDRs having the amino acid sequences of SEQ ID NOs: 1-3 or a conservative substitution variant of such amino acid sequence.

In some embodiments of any of the aspects, the antibody, antigen-binding fragment thereof, antigen reagent or CAR comprises light chain CDRs having the amino acid sequences of SEQ ID NOs: 4-6. In some embodiments of any of the aspects, the antibody, antigen-binding fragment thereof, antigen reagent or CAR comprises light chain CDRs having the amino acid sequences of SEQ ID NOs: 4-6 or a conservative substitution variant of such amino acid sequence.

In some embodiments of any of the aspects, the antibody, antigen-binding fragment thereof, antigen reagent or CAR comprises the heavy or light chain complementarity determining region (CDR)s as follows:
(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3. In some embodiments of any of the aspects, the antibody, antigen-binding fragment thereof, antigen reagent or CAR comprises the heavy or light chain complementarity determining region (CDR)s as follows:

(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2; and (f) a heavy chain CDR3 having the amino acid sequence of SEQ ID NO: 3; or a conservative substitution variant of the amino acid sequence of any of (a)-(f). In some embodiments of any of the aspects, the antibody, antibody reagent, antigen-binding portion thereof, or CAR that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

In some embodiments, the antibody, antibody reagent, antigen-binding portion thereof, or CAR can comprise one or more CDRs (e.g., one CDR, two CDRs, three CDRs, four CDRs, five CDRs, or six CDRs) having the sequence of a CDR selected from SEQ ID NOs: 1-6. In some embodiments, the antibody, antibody reagent, antigen-binding portion thereof, or CAR can comprise CDRs having the sequence of the CDRs of SEQ ID NOs: 1-6.

In some embodiments of any of the aspects, the antibody, antibody reagent, antigen-binding portion thereof, or CAR can comprise a heavy chain sequence having the amino acid sequence of SEQ ID NO: 36 and/or a light chain sequence having the amino acid sequence of SEQ ID NO: 38.

In one aspect of any of the embodiments, described herein is an antibody, antibody reagent, antigen-binding portion thereof, or CAR that specifically binds an CHI3L1 polypeptide, and can compete for binding of CHI3L1 with an antibody comprising light chain CDRs having the amino acid sequences of SEQ ID NOs: 4-6 and heavy chain CDRs having the amino acid sequences of SEQ ID NOs: 1-3. In some embodiments of any of the aspects, the antibody, antibody reagent, antigen-binding portion thereof, or CAR that specifically binds an CHI3L1 polypeptide binds specifically to an epitope selected from SEQ ID NOs: 13-24. In some embodiments of any of the aspects, the antibody, antibody reagent, antigen-binding portion thereof, or CAR that specifically binds an CHI3L1 polypeptide binds specifically to the epitope of SEQ ID NO: 13.

In some embodiments, the antibody, antibody reagent, antigen-binding portion thereof, and/or CAR as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., CHI3L1. A wide variety of PCR-based site-specific mutagenesis approaches are also known in the art and can be applied by the ordinarily skilled artisan.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., CHI3L1). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$ domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence. In some embodiments, a conservatively modified variant of an antibody reagent can comprise alterations other than in the CDRs, e.g., a conservatively modified variant of an antibody, antibody reagent, antigen-binding portion thereof, or CAR can comprise CDRs having the sequence of one or more of SEQ ID NOs 1-6. In some embodiments, a conservatively modified variant of an antibody, antibody reagent, antigen-binding portion thereof, or CAR can comprise CDRs having the sequences of SEQ ID NOs: 1-6.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody, antigen-binding portion thereof, or CAR as described herein comprises at least one CDR which is not identical to the sequence of SEQ ID NOs: 1-6, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments, a CAR comprises an extracellular domain comprising an anti-CHI3L1 antibody or antigen-binding portion thereof that binds one or more epitopes of a CHI3L1 polypeptide; a transmembrane domain, one or more intracellular co-stimulatory signaling domains, and a primary signaling domain. Exemplary anti-CHI3L1 antibodies and antigen-binding portions thereof, as well as exemplary epitopes, are described elsewhere herein As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain. CARs have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CD3ζ) signals upon antigen binding, "Second-generation" CARs include those that provide both costimulation (e.g., CD28 or CD 137) and activation (CD3ζ). "Third-generation" CARs include those that provide multiple costimulatory (e.g., CD28 and CD 137) domains and activation domains (e.g., CD3ζ). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In some embodiments of any of the aspects, a CAR comprises an extracellular binding domain that comprises a humanized CHI3L1-specific binding domain; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., CHI3L1. The binding domain may be derived either from a natural, synthetic, semi-synthetic, or recombinant source.

In some embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation. The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8a, CD4, CD28 and CD7, which may be wild-type hinge regions from these molecules or may be altered. In another embodiment, the hinge domain comprises a CD8a hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T-cell receptor, CD3ε, CD3, CD4, CD5, CD8a, CD9, CD 16, CD22, CD27, CD28, CD33, CD37, CD45, CD64, CD80, CD86, CD 134, CD137, CD152, CD 154, and PD1.

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3ζ primary signaling domain.

In some embodiments, an antibody-drug conjugate is provided. In particular embodiments, an antibody-drug conjugate comprises an antibody, antibody reagent, or antigen-binding portion thereof as described herein. The drug can be, e.g., a chemotherapeutic molecule as described elsewhere herein. In some embodiments, the antibody-drug conjugate comprises a chemotherapeutic agent directly conjugated and/or bound to an antibody or antigen-binding portion thereof. In some embodiments, binding can be non-covalent, e.g., by hydrogen bonding, electrostatic, or van der Waals interactions; however, binding may also be covalent. By "conjugated" is meant the covalent linkage of at least two molecules. In some embodiments, the composition can be an antibody-drug conjugate.

In some embodiments, an antibody, antibody reagent, or antigen-binding portion thereof can be bound to and/or conjugated to multiple chemotherapeutic molecules. In some embodiments, an antibody-drug conjugate can be bound to and/or conjugated to multiple chemotherapeutic molecules. In some embodiments, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats (See, e.g., Rockwood et al. Nature Protocols 2011 6:1612-1631 and US Patent Publications 2011/0167602; 2011/0009960; 2012/0296352; and U.S. Pat. No. 8,172,901; each of which is incorporated by reference herein in its entirety). The structure of the matrix can be selected by one of skill in the art depending upon the intended application of the composition, e.g., electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are super-absorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

In some embodiments, the technology described herein relates to a nucleic acid encoding an antibody, antibody reagent, antigen-binding portion thereof, or CAR as described herein. In some embodiments, the nucleic acid is a cDNA. In some embodiments, the one or more portions of nucleic acid encoding CDR(s) comprises a sequence selected from SEQ ID NOs: 7-12. In some embodiments, the nucleic acid can comprise SEQ ID NO: 37 and/or SEQ ID NO: 39.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode a monoclonal antibody molecule, antibody reagent, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

In some embodiments, a nucleic acid encoding an antibody, antibody reagent, antigen-binding portion thereof, or CAR as described herein is comprised by a vector. In some of the aspects described herein, a nucleic acid sequence encoding an antibody, antibody reagent, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In one aspect of any of the embodiments, described herein is a cell comprising an antibody, antibody reagent, antigen-binding portion thereof, or CAR as described herein, or a nucleic acid encoding such an antibody, antibody reagent, antigen-binding portion thereof, or CAR.

The expression of an antibody, antibody reagent, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli*, for example. Other gene expression elements useful for the expression of cDNA encoding antibodies, antigen-binding portions thereof, or CARs include, but are not limited to (a) viral transcription promoters and their enhancer elements, such as the SV40 early promoter, Rous sarcoma virus LTR, and Moloney murine leukemia virus; (b) splice regions and polyadenylation sites such as those derived from the SV40 late region, and (c) polyadenylation sites such as in SV40. Immunoglobulin cDNA genes can be expressed, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

A gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the genes encoding the antibody, antigen-binding portion thereof, CAR, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the genes can be assembled on the same expression vector.

For transfection of the expression vectors and production of the antibodies, antibody reagents, antigen-binding portions thereof, or CARs described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC # CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment, as known to one of ordinary skill in the art.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

In one aspect, a cell comprising an isolated antibody, antigen-binding portion thereof, or CAR as described herein is provided. In some embodiments, the isolated antibody, antigen-binding portion thereof, or CAR as described herein is expressed on the cell surface. In some embodiments, the cell comprises a nucleic acid encoding an isolated antibody, antigen-binding portion thereof, or CAR as described herein.

In some embodiments, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-CHI3L1 antibody or antigen binding portion thereof that binds a CHI3L1 polypeptide, with an intracellular signaling domain of CD3, CD28, 4-1BB, Ox40, or any combinations thereof. Thus, these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

In one aspect of any of the embodiments, described herein is a compositions comprising an antibody, antibody reagent, antigen-binding portion thereof, or CAR as described herein or a nucleic acid encoding an antibody, antibody reagent, antigen-binding portion thereof, or CAR as described herein or a cell as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody, antibody reagent, antigen-binding portion thereof, or CAR as described herein or a nucleic acid encoding an antibody, antibody reagent, antigen-binding portion thereof, or CAR as described herein can be a lyophilisate.

In some embodiments, the technology described herein relates to a syringe or catheter, including an organ-specific catheter (e.g., renal catheter, biliary catheter, cardiac catheter, etc.), comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malignancy, e.g., an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents In one aspect, described herein is a method of inhibiting or killing a CHI3L1+ cell, the method comprising contacting the cell with an isolated antibody, antibody reagent, antigen-binding portion thereof, or CAR as described herein, a nucleic acid encoding such polypeptides, a cell comprising such a polypeptide or nucleic acid, or a composition comprising such a polypeptide or nucleic acid. Inhibiting a CHI3L1+ cell can comprise inhibiting the metabolic activity, metastasis, and/or proliferation of the cell. Assays for measuring metabolic activity, metastasis (e.g., migration assays) and proliferation are well known in the art. Similarly, assays for measuring killing of CHI3L1+ cells, e.g., cell viability assays are well known in the art.

As used herein, a "CHI3L1+" cell is a cell expressing an increased level of CHI3L1+, e.g., as compared to a healthy cell of the same type or an average level of CHI3L1 found in healthy cells of the same type. In some embodiments, an increased level of CHI3L1 can be a level which is at least 1.5× the level found in a reference, e.g., 1.5×, 2×, 3×, 4×, 5× or greater than the reference level.

In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the subject is in need of treatment for a cancer and/or malignancy. In some embodiments, the subject is in need of treatment for: prostate cancer, colon cancer, rectal cancer, ovarian cancer, kidney cancer, breast cancer, glioblastoma, melanoma, malignant melanoma, and lung cancer. In some embodiments, the method is a method of treating a subject. In some embodiments, the method is a method of treating a cancer in a subject.

In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the method is a method of treating asthma. In some embodiments, the subject is in need of treatment for asthma.

Asthma refers to a chronic inflammatory disease of the respiratory system in which the airway occasionally constricts, becomes inflamed, and is lined with excessive amounts of mucus, often in response to one or more triggers. Asthma can be defined simply as reversible airway obstruction in an individual over a period of time. Asthma can be allergic/atopic or non-allergic. Asthma is characterized by the presence of cells such as eosinophils, mast cells, basophils, and activated T lymphocytes in the airway walls. With chronicity of the process, secondary changes occur, such as thickening of basement membranes and fibrosis. The disease is characterized by increased airway hyper responsiveness to a variety of stimuli, and airway inflammation and constriction. This airway narrowing causes symptoms such as wheezing, shortness of breath, chest tightness, and coughing. The airway constriction responds to bronchodilators. Between episodes, most patients feel well but can have mild symptoms and they can remain short of breath after exercise for longer periods of time than the unaffected individual. The symptoms of asthma can range from mild to life threatening.

Asthma can be triggered by such things as exposure to an allergen (allergic asthma), or non-allergens (non-allergic asthma) such as cold air, pollution (e.g., ozone), warm air, moist air, exercise or exertion, or emotional stress. In children, the most common triggers are viral illnesses such as those that cause the common cold (Zhao J., et. al., 2002, *J Pediatr. Allergy Immunol.* 13: 47-50).

Common allergens that trigger the allergic asthma include "seasonal" pollens, year-round dust mites, molds, pets, and insect parts, foods, such as fish, egg, peanuts, nuts, cow's milk, and soy, additives, such as sulfites, work-related agents, such as latex. Approximately 80% of children and 50% of adults with asthma also have allergies.

Common irritants that can trigger asthma in airways that are hyperreactive include respiratory infections, such as those caused by viral "colds," bronchitis, and sinusitis, medication drugs, such as aspirin, other NSAIDs (nonsteroidal antiinflammatory drugs), and beta blockers (used to treat blood pressure and other heart conditions), tobacco smoke, outdoor factors such as ozone, smog, weather changes, and diesel fumes; indoor factors such as paint, detergents, deodorants, chemicals, and perfumes; nighttime GERD (gastroesophageal reflux disorder); exercise, especially under cold dry conditions; work-related factors such as chemicals, dusts, gases, and metals; emotional factors, such as laughing, crying, yelling, and distress; and hormonal factors, such as in premenstrual syndrome.

Regardless of the trigger, asthma is associated with reversible airway obstruction and airway hyperreactivity (AHR), an increased sensitivity of the airways to nonspecific stimuli such as cold air or respiratory irritants, and can be quantitated by responsiveness to methacholine or histamine. A patient diagnosed as asthmatic will generally have multiple indications over time, including wheezing, asthmatic attacks, and a positive response to methacholine challenge, i.e., a PC20 on methacholine challenge of less than about 4 mg/ml. The basic diagnosis and measurement of asthma is peak flow rates and the following diagnostic criteria are used by the British Thoracic Society (Pinnock H., and Shah R., 2007, Br. Med. J. 334 (7598): 847-50): ≥20% difference on at least three days in a week for at least two weeks; ≥20% improvement of peak flow following treatment, for example: 10 minutes of inhaled β-agonist (e.g., salbutamol), six week of inhaled corticosteroid (e.g., beclometasone), and 14 days of 30 mg prednisolone; and ≥20% decrease in peak flow following exposure to a trigger (e.g., exercise). Further guidelines for diagnosis may be found, for example, in the National Asthma Education Program Expert Panel Guidelines for Diagnosis and Management of Asthma, National Institutes of Health, 1991, Pub. No. 91-3042.

As demonstrated herein, the antibodies, antibody reagents, and/or antigen-binding portions thereof which are described herein can prevent weight gain, e.g., when administered to subjects consuming high fat diet. Accordingly, administration of the the antibodies, antibody reagents, and/or antigen-binding portions thereof which are described herein are contemplated for use in methods of treating obesity, reducing weight gain, preventing weight gain, promoting weight loss, and the like. Such methods can, e.g., promote metabolic health, be pursued for aesthetic reasons, and/or prepare patients for surgical interventions which are counter indicated for those with high BMIs or weights.

In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the method is a method of treating obesity and/or preventing weight gain. In some embodiments, the subject is in need of treatment for obesity and/or weight gain. In some embodiments, the method is a method of treating NASH, NFALD, a fatty liver disease, and/or metabolic syndrome. In some embodiments, the subject is in need of treatment for NASH, NFALD, a fatty liver disease, and/or metabolic syndrome.

In one aspect, the technology described herein relates to a method of promoting weight and/or fat loss comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the subject is a subject in need of promotion of weight loss.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g. with age, gender, ethnicity, fitness, and body type, amongst other factors. In some embodiments, a subject with obesity can be a subject with a body mass index of at least about 25 kg/m$^2$ prior to administration of a treatment as described herein. In some embodiments, a subject with obesity can be a subject with a body mass index of at least about 30 kg/m$^2$ prior to administration of a treatment as described herein.

The term "nonalcoholic fatty liver disease" or "NAFLD" describes a wide spectrum of liver diseases ranging from simple fatty liver (steatosis) to nonalcoholic steatohepatitis (NASH) with progressive fibrosis and liver failure to cirrhosis. All of the stages of NAFLD have in common the accumulation of fat in the hepatocytes. In NASH, the fat accumulation is associated with varying degrees of inflammation (hepatitis) and scarring (fibrosis) of the liver. NAFLD and NASH can occur in individuals who do not consume excessive amounts of alcohol. Yet, in many respects, the histological picture of an NAFLD biopsy is similar to what can be seen in liver disease caused by alcohol abuse. NAFLD and NASH are considered the primary fatty liver diseases. The secondary fatty liver diseases include those that occur in other types of liver disease. Secondary fatty liver can also occur in chronic viral hepatitis C (HCV), chronic viral hepatitis B (HBV), chronic autoimmune hepatitis (AIH), and Wilson's disease.

Hyperglycemia with or without evidence of hyperlipidemia is commonly associated with NAFLD. The disease exhibits the histological features of alcohol-induced liver disease in patients who do not consume significant amounts of alcohol. All of the stages of NAFLD have in common the accumulation of fat in the liver cells. Farrell and Larter in Hepatology, 243:S99-S1 12 (2006) describe NASH as "the lynchpin" between hepatic steatosis and cirrhosis in the spectrum of NAFLD. See also, Palekar, et al., Liver mt., 26(2):151-6 (2006). In NASH, the fat accumulation of associated with varying degrees of inflammation and fibrosis. Conditions most commonly associated with NAFLD are obesity, type II diabetes and metabolic syndrome.

The symptoms of NAFLD and NASH can be identical. They are usually not dramatic and tend to be non-specific (as can also be observed in other diseases). The symptoms are minimal in most patients, who may, however, experience occasional, vague right upper-quadrant abdominal pain. This pain characteristically is dull and aching, without a predictable pattern of occurrence. It is not an intense, sudden, and severe pain, as might occur with, for example, gallstones. The abdominal pain in NAFLD and NASH is thought to be due to the stretching of the liver covering (capsule) when the liver enlarges and/or when there is inflammation in the liver. In contrast to ALD, hepatitis B, or hepatitis C, symptoms of severe, acute liver failure (e.g. jaundice, intense fatigue, loss of appetite, nausea, vomiting, and confusion) are not typically observed in NAFLD or NASH. Obesity and related conditions (e.g. diabetes, hypertension) are frequent seen among those suffering from NAFLD or NASH, and the classic signs of insulin resistance often dominate the physical exam in NAFLD and NASH. Acanthosis nigricans, a dark pigmentation of the skin of the armpits and neck can be a sign of insulin resistance and is frequently seen in children with NASH. When the liver is palpated, it usually feels normal. However, when very large amounts of fat accumulate in the liver, it can be become quite large with a soft, rounded edge that can be easily felt by the doctor.

In addition to the symptoms described above, a diagnosis of NAFLD or NASH is made based on the following criteria: clinical and/or biochemical signs of insulin resistance; biopsy; chronically elevated ALT; signs of fatty liver on ultrasound; exclusion of other causes of elevated ALT and fatty liver.

The term "steatosis" also referred to in the art as "fatty change" is the process referring to the abnormal retention of lipids within a cell. It reflects an impairment of the normal processes of synthesis and breakdown of triglyceride fat. Excess lipid accumulates in vesicles that displace the cytoplasm. When the vesicles are large enough to distort the nucleus, the condition is known as macrovesicular steatosis, otherwise the condition is known as microvesicular steatosis. Whilst not particularly detrimental to the cell in mild cases, large accumulations can disrupt cell constituents, and in severe cases the cell may even burst.

The term "metabolic syndrome" refers to a combination of risk factors for cardiovascular disease (CVD) identified in the National Cholesterol Education Program's Adult Treatment Panel III report. See for example the discussion by Grundy et al in Circulation, 109 (2004), 433-438 which is incorporated by reference herein in its entirety. The components of metabolic syndrome are: 1) abdominal obesity; 2) atherogenic dyslipidemia; 3) raised blood pressure; 4) insulin resistance; 5) proinflammatory state; and 6) prothrombotic state.

The term "fatty liver disease" as used herein refers to and comprises all kinds of disorders as a consequence of fat accumulation and/or fat infiltration into the liver that affect the anatomy, physiology, metabolism, and/or genetic activities of the liver, or that affect the generation of new liver cells and/or the regeneration of the liver, as a whole or parts thereof, transiently, temporarily, chronically or permanently, in a pathological way.

The term "liver disease" refers to disorders that affect the anatomy or metabolism of normal functioning of the liver. Liver diseases are caused by, for example, alcohol (e.g. ASH), non-alcoholic fatty liver changes (such as NAFLD including NASH), nutrition-mediated liver injury (for example starvation), other toxic liver injury (such as unspecific hepatitis induced by e.g. drugs such as but not limited to acetaminophen (paracetamol), chlorinated hydrocarbons (e.g. CC14), amiodarone (cordarone), valproate, tetracycline (only i.v.), isoniacid (Drug induced liver disease 2004. Lazerow S K, Abdi M S, Lewis J H. Curr Opin Gastroenterol., 2005, 21(3): 283-292), or food intoxication resulting in acute or chronic liver failure, e.g. by consumption of mushrooms containing aflatoxins (preferably B1 aflatoxin) or ingestion of certain metal (such as copper or cadmium) or herbal products used in natural medicine (hompeoatics such as Mild thistle, Chaparral, Kawa-Kawa), interference of bilirubin metabolism, hepatitis like syndromes, cholestasis, granulomatous lesions, intrahepatic vascular lesions and cirrhosis), trauma and surgery (e.g. Pringle maneuver), radiation-mediated liver injury (such as caused by radiotherapy).

In one aspect, described herein is a method of treating cancer in a subject in need thereof, the method comprising administering a cell as described herein, e.g., a cell comprising an antibody, antibody reagent, antigen-binding portion thereof, or CAR as described herein. In some embodiments, the cell is an immune cell.

In one aspect, described herein is a method of treating cancer in a subject in need thereof, the method comprising administering a nucleic acid as described herein or an immune cell comprising the nucleic acid to the subject, wherein the subject's immune cells are caused to express the polypeptide encoded by the nucleic acid. In some embodiments, the immune cell is a T cell. Nucleic acids can be targeted to particular cell types by, e.g., use of a cell-type specific promoter and/or a composition that selectively binds to the desired cell type. For example, conjugation of a nucleic acid to an aptamer can permit targeted delivery (McNamara, J O., et al. (2006) Nat. Biotechnol. 24:1005-1015). In an alternative embodiment, the nucleic acid can be delivered using drug delivery systems such as a nanoparticle, a dendrimer, a polymer, liposomes, or a cationic delivery system. Positively charged cationic delivery systems facilitate binding of an nucleic acid molecule (negatively charged) and also enhance interactions at the negatively charged cell membrane to permit efficient uptake of a nucleic acid by the cell. Cationic lipids, dendrimers, or polymers can either be bound to a nucleic acid, or induced to form a vesicle or micelle (see e.g., Kim S H., et al. (2008) Journal of Controlled Release 129(2):107-116) that encases a nucleic acid. The formation of vesicles or micelles further prevents degradation of the nucleic acid when administered systemically. Methods for making and administering cat-ionic-inhibitory nucleic acid complexes are well within the abilities of one skilled in the art. Some non-limiting examples of drug delivery systems useful for systemic delivery of nucleic acids include DOTAP Oligofectamine, "solid nucleic acid lipid particles", cardiolipin, polyethyleneimine, Arg-Gly-Asp (RGD) peptides, and polyamidoamines. In some embodiments, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira Pharmaceutical Res 2006 23:1631-1640; Soutschek et al., Nature 2004 432:173-8 and Lorenze et al. Bioorg. Med. Chem. Lett. 14, 4975-4977 (2004); each of which is incorporated by reference herein in its entirety. By way of example, the nucleic acid can be targeted to immune cells by encapsulating the inhibitor in a liposome comprising ligands of receptors expressed on immune cells, e.g., TCRs. In some embodiments, the liposome can comprise aptamers specific for immune cells.

In some embodiments, the methods described herein relate to CAR-T cell therapy. CAR-T cell and related therapies relate to adoptive cell transfer of immune cells (e.g., T cells) expressing a CAR that binds specifically to a targeted cell type (e.g., cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patients or subjects include any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g., a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an agent, including but not limited to, an antibody, antibody reagent, antigen-binding portion thereof, or CAR as described herein or a nucleic acid encoding an antibody, antibody reagent, antigen-binding portion thereof, or CAR, or a cell comprising such an agent, as described herein into a subject by a method or route which results in at least partial localization of the agents at a desired site. The pharmaceutical composition comprising an antibody, antibody reagent, antigen-binding portion thereof, or CAR as described herein or a nucleic acid encoding an antibody, antibody reagent, antigen-binding portion thereof, or CAR, or a cell comprising such an agent as described herein disclosed herein can be administered by any appropriate route which results in an effective treatment in the subject.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

It can generally be stated that a pharmaceutical composition comprising the cells, e.g., T cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{11}$ or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response. In some embodiments, the dosage can be from about $1\times10^5$ cells to about $1\times10^8$ cells per kg of body weight. In some embodiments, the dosage can be from about $1\times10^6$ cells to about $1\times10^7$ cells per kg of body weight. In some embodiments, the dosage can be about $1\times10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 μg/kg body weight to 100 μg/kg body weight. Alternatively, the dose range can be titrated to maintain serum levels between 1 μg/mL and 1000 μg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments, the doses are given once a day, or multiple times a day, for example but not limited to three times a day. In a some embodiments, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m$^2$ to about 700 mg/m$^2$. In some embodiments, the dose can be about 250 mg/m$^2$. In some embodiments, the dose can be about 375 mg/m$^2$. In some embodiments, the dose can be about 400 mg/m$^2$. In some embodiments, the dose can be about 500 mg/m$^2$.

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m$^2$ to about 400 mg/m$^2$ administered intravenously about every week. In some embodiments, the dose can be from about 200 mg/m$^2$ to about 400 mg/m$^2$ administered intravenously about every 2 weeks. In some embodiments, the dose can be from about 200 mg/m$^2$ to about 400 mg/m$^2$ administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds)). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach, i.e., adoptive immunothreapy.

In some embodiments, the methods described herein can further comprise administering an additional antibody, antibody reagent, antigen-binding portion thereof, or T cell comprising a CAR to the subject. In some embodiments, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for, e.g., cancer, can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

In one aspect, described herein is a method of detecting, prognosing, and/or diagnosing cancer or asthma, the method comprising detecting or measuring the level of CHI3L1 in a sample obtained from a subject by contacting the sample with an antibody, antibody reagent or antigen-binding portion thereof as described herein, wherein an increase in CHI3L1 levels relative to a reference level indicates the subject has cancer, is at increased risk of developing cancer or asthma.

In some embodiments of any of the aspects described herein, a subject administered a composition described herein can be a subject determined to have an elevated level of CHI3L1. In some embodiments, the elevated level of CHI3L1 is the level of circulating CHI3L1. In some embodiments of any of the aspects described herein, a subject administered a composition described herein can be a subject determined to have cancer cells which are CHI3L1+.

In some embodiments of any of the aspects described herein, the method comprising administering a composition as described herein can further comprise a first step of identifying a subject having an elevated level of CHI3L1. In some embodiments, the elevated level of CHI3L1 is the level of circulating CHI3L1. In some embodiments of any of the aspects described herein, the method comprising administering a composition as described herein can further comprise a first step of identifying a subject having cancer cells which are CHI3L1+.

In one aspect, described herein is an assay comprising contacting a test sample obtained from the subject with an antibody, antibody reagent, or antigen-binding portion thereof as described herein, and detecting the presence or intensity of a signal which indicates the presence or level of CHI3L1 in the sample; wherein an increase in the CHI3L1 level relative to a reference level indicates the subject has a higher risk of having or developing cancer.

In one aspect, described herein is a method of identifying a subject in need of treatment for cancer, the method comprising: contacting a test sample obtained from the subject with an antibody, antibody reagent, or antigen-binding portion thereof as described herein, detecting the presence or intensity of a signal which indicates the presence or level of CHI3L1 in the sample; and identifying the subject as being in need of treatment for cancer when the expression level CHI3L1 is increased relative to a reference level.

In one aspect, described herein is a method of determining if a subject is likely to respond to treatment with anti-CHI3L1 therapy, e.g., an anti-CHI3L1 antibody, antibody reagent, or antigen binding portion thereof, or T cell comprising a CAR that binds CHI3L1, the method comprising: contacting a test sample obtained from the subject with an antibody, antibody reagent, or antigen-binding portion thereof as described herein, detecting the presence or intensity of a signal which indicates the presence or level of CHI3L1 in the sample; determining that the subject is likely to respond to treatment with anti-CHI3L1 therapy when the level of CHI3L1 is increased relative to a reference level; and determining that the subject is not likely to respond to treatment with anti-CHI3L1 when the level of CHI3L1 is not increased relative to a reference level.

In one aspect, described herein is a method of treatment for cancer comprising; contacting a test sample obtained from the subject with an antibody, antibody reagent, or antigen-binding portion thereof as described herein; detecting the presence or intensity of a signal which indicates the presence or level of CHI3L1 in the sample; and treating the subject with an anti-CHI3L1 therapy when the level of CHI3L1 is increased relative to a reference level. In one aspect, described herein is a method of treating cancer comprising; administering a therapeutically effective amount of an anti-CHI3L1 therapy to a subject determined to be in need of treatment for cancer and further determined to have a level of CHI3L1 that is increased relative to a reference level, wherein the anti-CHI3L1 therapy comprises an antibody, antibody reagent, antigen-binding portion thereof, or T cell comprising a CAR that recognizes CHI3L1; nucleic acid; cell; or composition as described herein.

In one aspect, described herein is a method of detecting CHI3L1, the method comprising contacting a biological sample with an antibody, antibody reagent, or antigen-binding portion thereof as described herein, wherein reaction of the antibody or antigen-binding portion thereof with CHI3L1 indicates the presence of CHI3L1.

In some embodiments, the expression level of CHI3L1 can be measured by determining the level of an expression product of the CHI3L1 gene, e.g., a CHI3L1 RNA transcript or a CHI3L1 polypeptide. Such molecules can be isolated, derived, or amplified from a biological sample, such as a biofluid. In some embodiments, a detectable signal is generated by the antibody or antigen-binding portion thereof when a CHI3L1 molecule is present. In some embodiments, the antibody or antigen-binding portion thereof is detectably labeled or capable of generating a detectable signal. In some embodiments, the level of the CHI3L1 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluoresence assay; mass spectroscopy; FACS; and immunoelectrophoresis assay. In some embodiments, the antibody or antigen-binding portion thereof is detectably labeled or generates a detectable signal. In some embodiments, the expression level of CHI3L1 is normalized relative to the expression level of one or more reference genes or reference proteins. In some embodiments, the reference level of CHI3L1 is the expression level of CHI3L1 in a prior sample obtained from the subject.

In some embodiments, the level of CHI3L1 can be the level of CHI3L1 polypeptide. Detection of CHI3L1 polypeptides can be according to any method known in the art.

Immunological methods to detect CHI3L1 polypeptides in accordance with the present technology include, but are not limited to antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, a CHI3L1 polypeptide. In some embodiments, the assays, methods, and/or systems described herein can comprise: an anti-CHI3L1 antibody reagent. In some embodiments, the antibody reagent can be detectably labeled. In some embodiments, the antibody reagent can be attached to a solid support (e.g., bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., CHI3L1). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a CHI3L1 molecule. Between each step the plate is typically washed with a mild detergent solution to remove any proteins or antibodies that are not specifically bound. After the final wash step the plate is developed by adding an enzymatic substrate to produce a visible signal, which indicates the quantity of CHI3L1 polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of CHI3L1 polypeptide in a sample. LFIAs are a simple device intended to detect the presence (or absence) of CHI3L1 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of CHI3L1 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a CHI3L1-specific antibody reagent). The test line will also contain antibody reagents (e.g., a CHI3L1-specific antibody reagent). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of CHI3L1 polypeptides. In some embodiments, the dip stick (or LFIA) can be suitable for use with urine samples. In some embodiments, a dip stick can be suitable for use with blood samples.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of CHI3L1 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010); Lin and Prichard "Handbook of Practical Immunohistochemistry" Springer (2011); which are incorporated by reference herein in their entireties. In some embodiments, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in Burry "Immunocytochemistry: A Practical Guide for Biomedical Research" Springer (2009); which is incorporated by reference herein in its entirety.

In some embodiments, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is labeled with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfluorescein (commonly known by the abbreviations FAM and F), 6-carboxy-2',4', 7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes.

In some embodiments, a detectable label can be a radiolabel including, but not limited to $^{3}H$, $^{124}I$, $^{35}S$, $^{14}C$, $^{32}P$, and $^{33}P$.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif.

An antibody reagent can also be detectably labeled using fluorescence emitting metals such as $^{152}Eu$, or others of the lanthanide series. These metals can be attached to the antibody reagent using such metal chelating groups as diethylenetriaminepentaacetic acid (DTPA) or ethylenediaminetetraacetic acid (EDTA).

The assays and methods as described herein can relate to determining if a subject has an increased level of CHI3L1 relative to a reference level. In some embodiments, the reference level of CHI3L1 can be the level of CHI3L1 in a healthy subject not having, or not diagnosed as having, e.g., cancer. In some embodiments, the reference level can be the level in a sample of similar cell type, sample type, sample processing, and/or obtained from a subject of similar age, sex and other demographic parameters as the sample/subject for which the level of CHI3L1 is to be determined. In some embodiments, the test sample and control reference sample are of the same type, that is, obtained from the same biological source, and comprising the same composition, e.g., the same number and type of cells and/or type of sample material. Accordingly, in some embodiments, the level of CHI3L1 which is increased can vary as demographic factors such as age, gender, genotype, environmental factors, and individual medical histories vary. In some embodiments, the reference level can comprise the level of CHI3L1 (e.g., CHI3L1 polypeptide) in a sample of the same type taken from a subject not exhibiting any signs or symptoms of, e.g., cancer. In some embodiments, the reference expression level of CHI3L1 can be the expression level of CHI3L1 in a prior sample obtained from the subject. This permits a direct analysis of any change in levels in that individual.

In some embodiments, a level of CHI3L1 can be increased relative to a reference level if the level of CHI3L1 is at least 1.25× the reference level, e.g., at least 1.25×, at least 1.5×, at least 2×, at least 3×, at least 4×, at least 5×, at least 6×, or greater of the reference level. In some embodiments, the expression level of CHI3L1 can be normalized relative to the expression level of one or more reference genes or reference proteins. In some embodiments, the expression level of CHI3L1 can be normalized relative to a reference value.

In some embodiments, the expression level of no more than 20 other genes is determined. In some embodiments, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodiments, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of CHI3L1 as described herein.

In some embodiments, the methods, assays, and systems described herein can further comprise a step of obtaining a test sample from a subject. In some embodiments, the subject can be a human subject.

In some embodiments, the methods, assays, and systems described herein can comprise creating a report based on the level of CHI3L1. In some embodiments, the report denotes raw values for CHI3L1 in the test sample (plus, optionally, the level of CHI3L1 in a reference sample) or it indicates a percentage or fold increase in CHI3L1 as compared to a reference level, and/or provides a signal that the subject is at risk of having, or not having cancer.

As used herein "at risk of having" refers to at least a 2-fold greater likelihood of having a particular condition as compared to a subject that did not have an elevated and/or increased level of CHI3L1, e.g., a 2-fold, or 2.5-fold, or 3-fold, or 4-fold, or greater risk.

In some embodiments, the assay or method can further comprise the step of administering an anti-CHI3L1 therapy. In some embodiments, the anti-CHI3L1 therapy comprises an isolated antibody, antibody reagent, antigen-binding portion thereof, or CAR or CAR T cell; nucleic acid; cell; or composition as described herein.

In one aspect of any of any of the embodiments, described herein is an antibody, antibody reagent, or antigen-binding portion thereof as described herein conjugated to or coupled to a detectable label.

In one aspect of any of any of the embodiments, described herein is a solid support comprising an antibody, antibody reagent, antigen-binding fragment thereof as described herein. In some embodiments of any of the aspects, the antibody, antibody reagent or antigen-binding fragment thereof is detectably labeled. In some embodiments of any of the aspects, the solid support comprises a particle, a bead, a polymer, or a substrate.

In one aspect of any of the embodiments, described herein is a molecular complex comprising at least one antibody, antibody reagent, antigen-binding fragment thereof, or CAR of as described herein bound to an CHI3L1 polypeptide.

In one aspect, described herein is a kit comprising a composition as described herein, e.g., a composition comprising an antibody, antibody reagent, antigen-binding portion thereof, or CAR as described herein. A kit is any manufacture (e.g., a package or container) comprising at least one reagent, e.g., an antibody, the manufacture being promoted, distributed, or sold as a unit for performing the methods described herein. In some embodiments of any of the aspects, the antibody, antibody reagent, antigen-binding fragment thereof as described herein is immobilized on a solid support. In some embodiments of any of the aspects, the solid support comprises a particle, a bead, a polymer, or a substrate. In some embodiments of any of the aspects, the antibody, antibody reagent or antigen-binding fragment thereof is detectably labeled.

The kits described herein can optionally comprise additional components useful for performing the methods described herein. By way of example, the kit can comprise fluids (e.g., buffers) suitable for composition comprising an antibody, antigen-binding portion thereof, or CAR as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticaly significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g. an antibody or antibody reagent) is comprised by a vector. In some of the aspects described herein, a nucleic acid sequence encoding a given polypeptide as described herein, or any module thereof, is operably linked to a vector. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more. In some embodiments, the antibody, antigen-binding portion thereof, or CAR described herein is isolated. In some embodiments, the antibody, antibody reagent, antigen-binding portion thereof, or CAR described herein is purified.

As used herein, "engineered" refers to the aspect of having been manipulated by the hand of man. For example, an antibody, antibody reagent, antigen-binding portion thereof, or CAR is considered to be "engineered" when the sequence of the antibody, antibody reagent, antigen-binding portion thereof, or CAR is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-8}$ to $10^{-12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ $M^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an peptide (e.g., an antibody, CAR or portion thereof) described herein to bind to a target, such as an antigen present on the cell-surface of a cancer cell, with a KD $10^{-5}$M (10000 nM) or less, e.g., $10^{-6}$ M, $10^{-7}$M, $10^{-8}$ M, $10^{-9}$M, $10^{-10}$ M, $10^{-11}$M, $10^{-12}$M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, or CAR is said to specifically bind an antigen when it preferentially recognizes its target antigen in a complex mixture of proteins and/or macromolecules.

In some embodiments, an antibody, antigen-binding portion thereof, and/or CAR as described herein binds to CHI3L1 with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an antibody, antigen-binding portion thereof, and/or CAR as described herein binds to CHI3L1 with a dissociation constant ($K_D$) of from about $10^{-5}$ M to $10^{-6}$ M. In some embodiments, an antibody, antigen-binding portion thereof, and/or CAR as described herein binds to CHI3L1 with a dissociation constant ($K_D$) of from about $10^{-6}$ M to $10^{-7}$ M. In some embodiments, an antibody, antigen-binding portion thereof, and/or CAR as described herein binds to CHI3L1 with a dissociation constant ($K_D$) of from about $10^{-7}$ M to $10^{-8}$ M. In some embodiments, an antibody, antigen-binding portion thereof, and/or CAR as described herein binds to CHI3L1 with a dissociation constant (KD) of from about $10^{-8}$ M to $10^{-9}$ M. In some embodiments, an antibody, antigen-binding portion thereof, and/or CAR as described herein binds to CHI3L1 with a dissociation constant (KD) of from about $10^{-9}$ M to $10^{-10}$ M. In some embodiments, an antibody, antigen-binding portion thereof, and/or CAR as described herein binds to CHI3L1 with a dissociation constant (KD) of from about $10^{-10}$ M to $10^{-11}$ M. In some embodiments, an antibody, antigen-binding portion thereof, and/or CAR as described herein binds to CHI3L1 with a dissociation constant (KD) of from about $10^{-11}$ M to $10^{-12}$ M. In some embodiments, an antibody, antigen-binding portion thereof, and/or CAR as described herein binds to CHI3L1 with a dissociation constant ($K_D$) of less than $10^{-12}$ M.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADAM Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An antibody, antibody reagent, antigen-binding fragment thereof, or chimaeric antigen receptor (CAR), that specifically binds an CHI3L1 polypeptide, said antibody reagent, antigen-binding portion thereof, or CAR comprising at least one heavy or light chain complementarity determining region (CDR) selected from the group consisting of:
   (a) a light chain CDR1 having the amino acid sequence of SEQ ID NO: 4;
   (b) a light chain CDR2 having the amino acid sequence of SEQ ID NO: 5;
   (c) a light chain CDR3 having the amino acid sequence of SEQ ID NO: 6;
   (d) a heavy chain CDR1 having the amino acid sequence of SEQ ID NO: 1;
   (e) a heavy chain CDR2 having the amino acid sequence of SEQ ID NO: 2; and
   (f) a heavy chain CDR3 having the amino acid sequence of SEQ ID NO: 3; or a conservative substitution variant of one or more of (a)-(f).

2. The antibody, antibody reagent, antigen-binding portion thereof, or CAR of paragraph 1, which comprises heavy chain CDRs having the amino acid sequences of SEQ ID NOs: 1-3 or a conservative substitution variant of such amino acid sequence.

3. The antibody, antibody reagent, antigen-binding portion thereof, or CAR of any of paragraphs 1-2, which comprises light chain CDRs having the amino acid sequences of SEQ ID NOs: 4-6 or a conservative substitution variant of such amino acid sequence.

4. The antibody, antibody reagent, antigen-binding portion thereof, or CAR of any of paragraphs 1-3, which comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

5. An antibody, antibody reagent, antigen-binding portion thereof, or CAR that specifically binds an CHI3L1 polypeptide, and can compete for binding of CHI3L1 with an antibody comprising light chain CDRs having the amino acid sequences of SEQ ID NOs: 4-6 and heavy chain CDRs having the amino acid sequences of SEQ ID NOs: 1-3.

6. The antibody, antibody reagent, antigen-binding portion thereof, or CAR of paragraph 5, wherein the antibody, antibody reagent or antigen-binding fragment thereof binds to the epitope of SEQ ID NO: 13.

7. An antibody, antibody reagent, antigen-binding portion thereof, or CAR of paragraphs 5 or 6, wherein the antibody, antibody reagent or antigen-binding fragment thereof binds a CHI3L1 polypeptide at an eptitope selected from SEQ ID NOs: 13-24.

8. The antibody, antibody reagent, antigen-binding portion thereof, or CAR of any of paragraphs 1-7, further comprising a conservative substitution in a sequence not comprised by a CDR.

9. The antibody, antibody reagent, antigen-binding portion thereof, or CAR of any of paragraphs 1-8, wherein the antibody reagent or antigen-binding fragment thereof is fully human or fully humanized.

10. The antibody, antibody reagent, antigen-binding portion thereof, or CAR of any of paragraphs 1-9, wherein the antibody reagent or antigen-binding fragment thereof is fully humanized except for the CDR sequences.

11. The antibody, antibody reagent, antigen-binding portion thereof, or CAR of any of paragraphs 1-10, wherein the reagent or fragment is selected from the group consisting of:
an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

12. A composition comprising the antibody, antibody reagent, antigen-binding portion thereof, or CAR of any one of paragraphs 1-11, and a chemotherapeutic agent.

13. The composition of paragraph 12, wherein the antibody, antibody reagent, or antigen-binding portion thereof is conjugated to the chemotherapeutic agent.

14. A nucleic acid sequence encoding the antibody, antibody reagent, antigen-binding fragment thereof, or CAR of any of paragraphs 1-11, wherein at least one CDR is encoded by a nucleic acid sequence selected from SEQ ID NOs: 7-12.

15. A cell comprising the antibody, antibody reagent, antigen-binding fragment thereof, or CAR of any of paragraphs 1-11 or the nucleic acid sequence of paragraph 14.

16. A pharmaceutical composition comprising the antibody, antibody reagent, antigen-binding fragment thereof, or CAR of any of paragraphs 1-11; or the composition of any of paragraphs 12-13; or the cell of paragraph 15, and a pharmaceutically acceptable carrier.

17. A solid support comprising the antibody, antibody reagent, antigen-binding fragment thereof, or CAR of any of paragraphs 1-11.

18. The solid support of paragraph 17, wherein the antibody, antibody reagent or antigen-binding fragment thereof is detectably labeled.

19. The solid support of any of paragraphs 17-18, wherein the solid support comprises a particle, a bead, a polymer, or a substrate.

20. A kit for the detection of CHI3L1 polypeptide in a sample, the kit comprising at least a first antibody, antibody reagent, antigen-binding fragment thereof, or CAR of any of paragraphs 1-11 immobilized on a solid support and comprising a detectable label.

21. A molecular complex comprising at least one antibody, antibody reagent, antigen-binding fragment thereof, or CAR of any of paragraphs 1-11 bound to a CHI3L1 polypeptide.

22. A method of treating cancer in a subject in need thereof, the method comprising administering the antibody, antibody reagent, antigen-binding fragment thereof, or CAR of any of paragraphs 1-11; or the composition of any of paragraphs 12-13; or the cell of paragraph 15, to the subject.

23. The method of paragraph 22, wherein the cancer is primary cancer.

24. The method of paragraph 22, wherein the cancer is malignant cancer.

25. The method of any of paragraphs 22-24, wherein the cancer is selected from the group consisting of:
prostate cancer, colon cancer, rectal cancer, ovarian cancer, kidney cancer, breast cancer, glioblastoma, melanoma, malignant melanoma, and lung cancer.

26. A method of treating asthma in a subject in need thereof, the method comprising administering the antibody, antibody reagent, antigen-binding fragment thereof, or CAR of any of paragraphs 1-11; or the composition of any of paragraphs 12-13; or the cell of paragraph 15, to the subject.

27. The method of any of paragraphs 22-26 wherein the subject is a subject determined to have an elevated level of CHI3L1.

28. The method of paragraph 27, wherein the CHI3L1 is circulating CHI3L1.

Some embodiments of the technology described herein can be defined according to any of the following numbered paragraphs:

1. An antibody, antibody reagent, antigen-binding fragment thereof, or chimaeric antigen receptor (CAR), that specifically binds an CHI3L1 polypeptide, said antibody reagent, antigen-binding portion thereof, or CAR comprising at least one heavy or light chain complementarity determining region (CDR) selected from the group consisting of:
(a) a light chain CDR1 having the amino acid sequence of SEQ ID NO: 4;
(b) a light chain CDR2 having the amino acid sequence of SEQ ID NO: 5;
(c) a light chain CDR3 having the amino acid sequence of SEQ ID NO: 6;
(d) a heavy chain CDR1 having the amino acid sequence of SEQ ID NO: 1;
(e) a heavy chain CDR2 having the amino acid sequence of SEQ ID NO: 2; and
(f) a heavy chain CDR3 having the amino acid sequence of SEQ ID NO: 3; or a conservative substitution variant of one or more of (a)-(f).

2. The antibody, antibody reagent, antigen-binding portion thereof, or CAR of paragraph 1, which comprises heavy chain CDRs having the amino acid sequences of SEQ ID NOs: 1-3 or a conservative substitution variant of such amino acid sequence.

3. The antibody, antibody reagent, antigen-binding portion thereof, or CAR of any of paragraphs 1-2, which comprises light chain CDRs having the amino acid sequences of SEQ ID NOs: 4-6 or a conservative substitution variant of such amino acid sequence.

4. The antibody, antibody reagent, antigen-binding portion thereof, or CAR of any of paragraphs 1-3, which comprises light chain CDRs having the amino acid sequences of SEQ ID NOs: 4-6 and heavy chain CDRs having the amino acid sequences of SEQ ID NOs: 1-3 or a conservative substitution variant of such amino acid sequence.

5. The antibody, antibody reagent, antigen-binding portion thereof, or CAR of any of paragraphs 1-3, comprising a heavy chain sequence having the amino acid sequence of SEQ ID NO: 36.

6. The antibody, antibody reagent, antigen-binding portion thereof, or CAR of any of paragraphs 1-3, comprising a light chain sequence having the amino acid sequence of SEQ ID NO: 38.

7. The antibody, antibody reagent, antigen-binding portion thereof, or CAR of any of paragraphs 1-3, comprising a heavy chain sequence having the amino acid sequence of SEQ ID NO: 36 and a light chain sequence having the amino acid sequence of SEQ ID NO: 38.

8. An antibody, antibody reagent, antigen-binding portion thereof, or CAR that specifically binds an CHI3L1 polypeptide, and can compete for binding of CHI3L1 with an antibody comprising light chain CDRs having the amino acid sequences of SEQ ID NOs: 4-6 and heavy chain CDRs having the amino acid sequences of SEQ ID NOs: 1-7.

9. The antibody, antibody reagent, antigen-binding portion thereof, or CAR of paragraph 8, wherein the antibody, antibody reagent or antigen-binding fragment thereof binds to an epitope of SEQ ID NO: 13-24.

10. The antibody, antibody reagent, antigen-binding portion thereof, or CAR of paragraph 8, wherein the antibody, antibody reagent or antigen-binding fragment thereof binds to the epitope of SEQ ID NO: 13.

11. An antibody, antibody reagent, antigen-binding portion thereof, or CAR that specifically binds an CHI3L1 polypeptide at an epitope of SEQ ID NO: 13-24.

12. The antibody, antibody reagent, antigen-binding portion thereof, or CAR of any of paragraphs 1-11, further comprising a conservative substitution in a sequence not comprised by a CDR.

13. The antibody, antibody reagent, antigen-binding portion thereof, or CAR of any of paragraphs 1-12, wherein the antibody reagent or antigen-binding fragment thereof is fully human or fully humanized.

14. The antibody, antibody reagent, antigen-binding portion thereof, or CAR of any of paragraphs 1-13, wherein the antibody reagent or antigen-binding fragment thereof is fully humanized except for the CDR sequences.

15. The antibody, antibody reagent, antigen-binding portion thereof, or CAR of any of paragraphs 1-14, wherein the reagent or fragment is selected from the group consisting of:
an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.

16. A composition comprising the antibody, antibody reagent, antigen-binding portion thereof, or CAR of any one of paragraphs 1-15, and a chemotherapeutic agent.

17. The composition of paragraph 16s, wherein the antibody, antibody reagent, or antigen-binding portion thereof is conjugated to the chemotherapeutic agent.

18. A nucleic acid sequence encoding the antibody, antibody reagent, antigen-binding fragment thereof, or CAR of any of paragraphs 1-17.

19. A nucleic acid sequence encoding the antibody, antibody reagent, antigen-binding fragment thereof, or CAR of any of paragraphs 1-15, wherein at least one CDR is encoded by a nucleic acid sequence selected from SEQ ID NOs: 7-12.

20. The nucleic acid sequence of paragraph 18, comprising one or more sequences selected from SEQ ID NOs: 37 and/or 39.

21. A cell comprising the antibody, antibody reagent, antigen-binding fragment thereof, or CAR of any of paragraphs 1-15 or the nucleic acid sequence of any of paragraphs 18-20.

22. A pharmaceutical composition comprising the antibody, antibody reagent, antigen-binding fragment thereof, or CAR of any of paragraphs 1-15; or the composition of any of paragraphs 16-17; or the cell of paragraph 21, and a pharmaceutically acceptable carrier.

23. A solid support comprising the antibody, antibody reagent, antigen-binding fragment thereof, or CAR of any of paragraphs 1-15.

24. The solid support of paragraph 23, wherein the antibody, antibody reagent or antigen-binding fragment thereof is detectably labeled.

25. The solid support of any of paragraphs 23-24, wherein the solid support comprises a particle, a bead, a polymer, or a substrate.

26. A kit for the detection of CHI3L1 polypeptide in a sample, the kit comprising at least a first antibody, antibody reagent, antigen-binding fragment thereof, or CAR of any of paragraphs 1-15 immobilized on a solid support and comprising a detectable label.

27. A molecular complex comprising at least one antibody, antibody reagent, antigen-binding fragment thereof, or CAR of any of paragraphs 1-15 bound to a CHI3L1 polypeptide.

28. A method of treating cancer in a subject in need thereof, the method comprising administering the antibody, antibody reagent, antigen-binding fragment thereof, or CAR of any of paragraphs 1-15; or the composition of any of paragraphs 16-17; or the cell of paragraph 201, to the subject.

29. The method of paragraph 28, wherein the cancer is primary cancer.

30. The method of paragraph 28, wherein the cancer is malignant cancer.

31. The method of any of paragraphs 28-30, wherein the cancer is selected from the group consisting of:
prostate cancer, colon cancer, rectal cancer, ovarian cancer, kidney cancer, breast cancer, glioblastoma, melanoma, malignant melanoma, and lung cancer.

32. A method of treating asthma in a subject in need thereof, the method comprising administering the antibody, antibody reagent, antigen-binding fragment thereof, or CAR of any of paragraphs 1-15; or the composition of any of paragraphs 16-17; or the cell of paragraph 21, to the subject.

33. A method of treating obesity and/or preventing weight gain in a subject in need thereof, the method comprising administering the antibody, antibody reagent, antigen-binding fragment thereof, or CAR of any of paragraphs 1-15; or the composition of any of paragraphs 16-17; or the cell of paragraph 21, to the subject.

34. A method of promoting weight or fat loss in a subject in need thereof, the method comprising administering the antibody, antibody reagent, antigen-binding fragment thereof, or CAR of any of paragraphs 1-15; or the composition of any of paragraphs 16-17; or the cell of paragraph 21, to the subject.

35. A method of treating NASH, NFALD, or metabolic syndrome in a subject in need thereof, the method comprising administering the antibody, antibody reagent, antigen-binding fragment thereof, or CAR of any of paragraphs 1-15; or the composition of any of paragraphs 16-17; or the cell of paragraph 21, to the subject.

36. The method of any of paragraphs 28-35, wherein the subject is a subject determined to have an elevated level of CHI3L1.
37. The method of paragraph 36, wherein the CHI3L1 is circulating CHI3L1.

EXAMPLES

Example 1

Chitinase 3-Like-1 (Chi3l1) Neutralizing Antibodies as Therapeutics in Asthma and Lung Cancer Members of the 18 glycosyl hydrolase (GH) gene family are dysregulated in and play an important role in the pathogenesis of a variety of diseases. This is particularly striking for the chitinase-like protein called chitinase 3-like-1 (Chi3l1; also called Chil1 in mice and YKL-40 in man) in asthma and lung cancer.

It has been demonstrated that the levels of circulating Chi3l1 are increased in human asthma where they correlate with disease severity (1-4). Single nucleotide polymorphisms of Chi3l1 that correlate with increased levels of circulating Chi3l1, asthma prevalence and poor lung function have been identified (2, 3, 5). In accord with the items noted above, it was also demonstrated that null mutations of Chi3l1 markedly decreased Th2 inflammation and eosinophil accumulation in aeroallergen murine asthma models (6).

The levels of circulating YKL-40 are increased in many malignancies including cancers of the prostate, colon, rectum, ovary, kidney, breast, glioblastomas and malignant melanoma (7-19). In these diseases, the levels of YKL-40 frequently correlate directly with disease progression and inversely with disease-free interval and survival (7-19). This is particularly striking in lung cancer where the serum and tissue levels of YKL-40 are impressively increased and correlate with adverse outcomes (20-23). To address the roles of Chi3l1 in these responses, the roles of Chi3l1 in primary and metastatic lung cancer were evaluated. These studies demonstrate that (1) YKL-40 is expressed in an exaggerated manner in human lung cancer where it correlates inversely with survival; (2) in murine models, Chi3l1 is sequentially induced in normal peritumor and tumor tissues during the early and later stages, respectively, of lung cancer development; (3) Chi3l1 induction via a semaphorin 7a-dependent mechanism plays a critical role in the generation of a metastasis permissive pulmonary microenvironment; (4) in metastatic models, Chi3l1 production and metastatic spread can be inhibited via RIG-like helicase (RLH) innate immunity (24, 25). These studies demonstrate that Chi3l1 is induced in selective tissue compartments during lung cancer initiation and progression and define the essential role that it plays in disease progression.

Generation and Characterization of Antibody-Based Anti-Chi3l1 Based Therapeutics.

Because Chi3l1 is induced in patients with asthma and lung cancer and plays a critical role in the pathogenesis of murine models of both diseases studies were undertaken to develop and assess the efficacy of Chi3l1 neutralizing antibodies. Epitopes of Chi3l1 were selected (see Tables 1 and 2 for epitope design and selection) and monoclonal antibodies were generated.

Figure 2A:
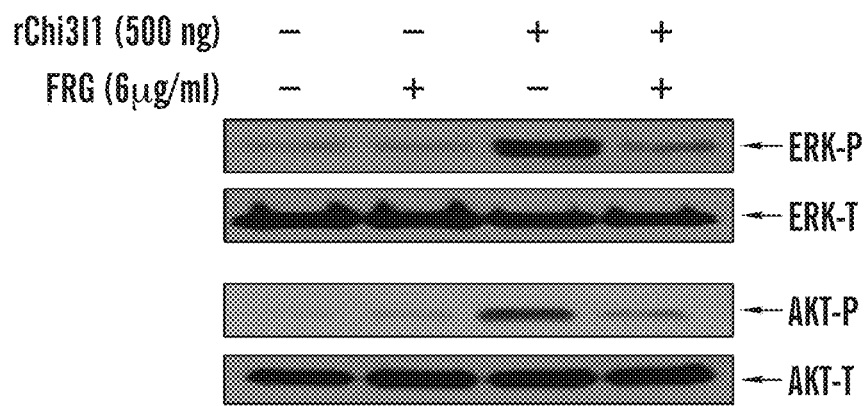
FIGS. 2A-2B demonstrate the neutralizing effects of FRG on Chi3l1-stimulated signaling.
Figure 2B:
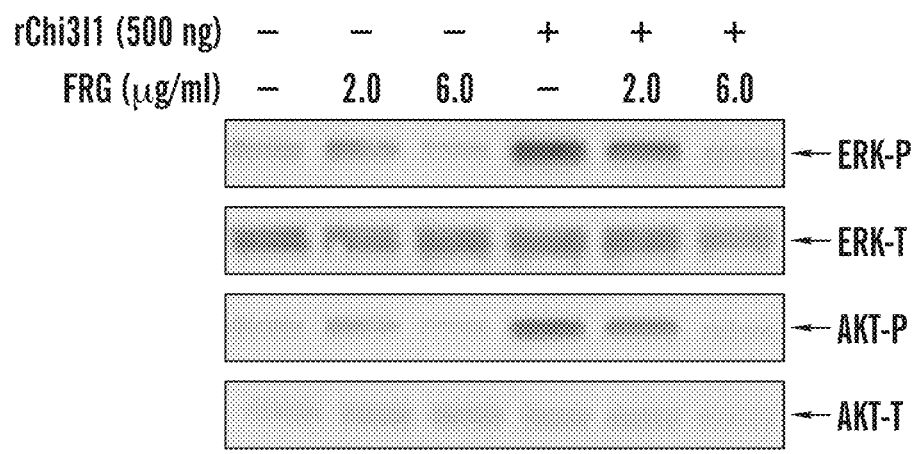

The antibodies were then assessed for their (a) sensitivity and specificity of detection of Chi3l1 in human and murine systems using denatured and non-denatured Chi3l1; (b) binding affinity; (c) ability to neutralize the effects of rChi3l1 in cell based assays; and (d) ability to neutralize Chi3l1 in vivo. Among the antibodies that were generated one, called FRG, had the most exciting characteristics. It is an IgG2b Kappa antibody that powerfully detects human and murine Chi3l1 under denaturing and non-denaturing conditions with high specificity (FIGS. 1A-1D). It also blocks rChi3l1 induced MAPK and AKT signaling in vitro (FIGS. 2A-2B).

Figure 3:
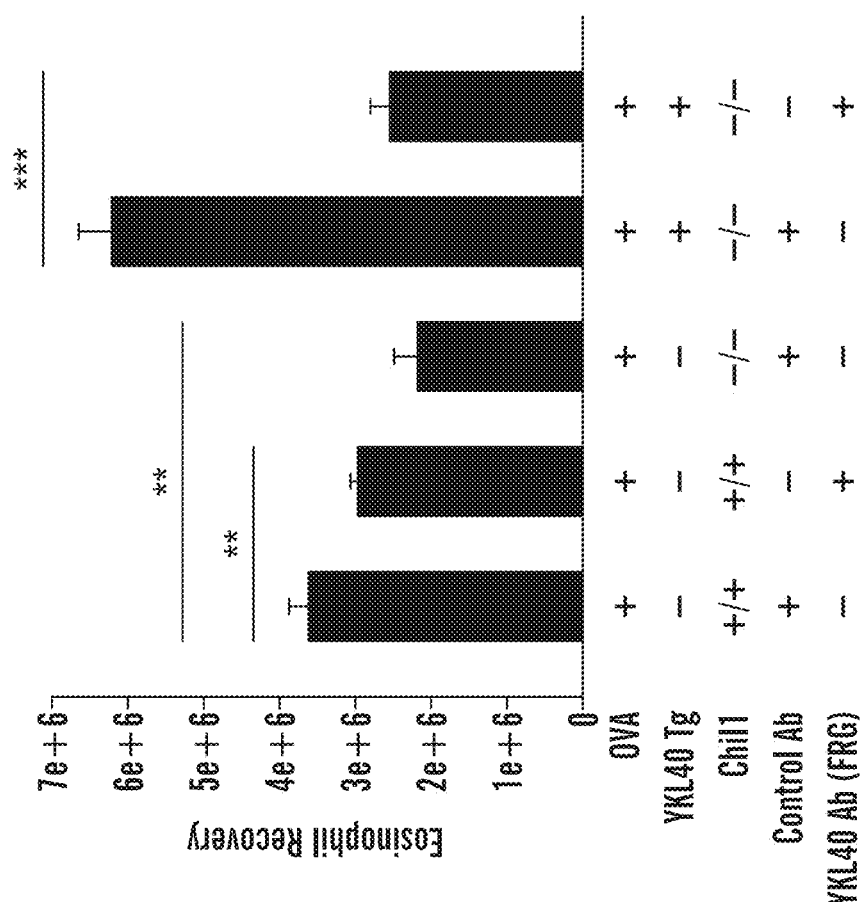
FIG. 3 depicts graphs of the effects of FRG on allergen-stimulated lung inflammation.

To determine if FRG blocked asthma-like inflammation, the ovalbumin sensitization and challenge murine model was utilized. Wild type mice and mice in which murine Chi3l1 (Chil1) was replaced by Chi3l1/YKL-40 were employed. The effects on airway eosinophilic inflammation were assessed in mice that received an IgG2b control antibody or FRG at a dose of 200 μg/mouse. As can be seen in FIG. 3, FRG was a potent inhibitor of aeroallergen-induced eosinophilic inflammation and BAL accumulation.

Figure 4:
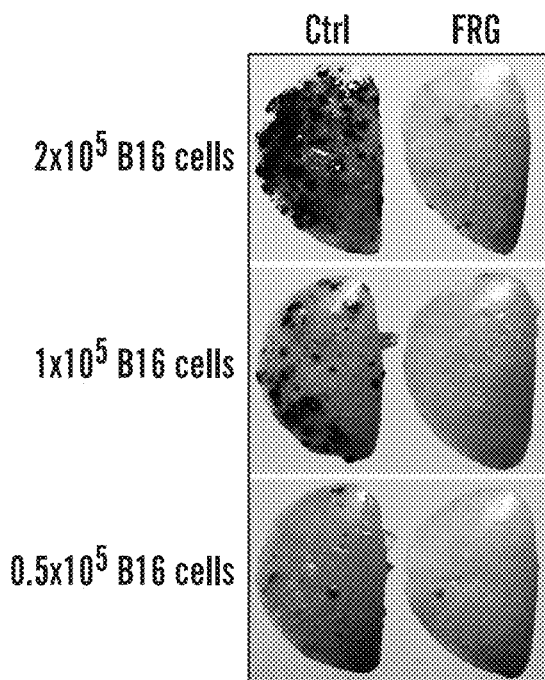
FIG. 4 depicts the effects of FRG on melanoma metastasis. Mice received B16-F10 cells by tail vein injection and were treated with control IGg2b antibody or FRG (200 µg/per mouse) every other day. The mice were sacrificed after 14 days and metastasis were evaluated.

To determine if FRG blocked metastatic cancer B16-F10 malignant melanocytes were used as described previously (24, 25). These cells were administered by tail vein to wild type mice and pulmonary metastasis were quantitated. Melanoma metastasis were assessed in mice that received an IgG2b control antibody or FRG at a dose of 200 μg/mouse. As can be seen in FIG. 4, FRG was a potent inhibitor of melanoma metastasis. Importantly, these effects were not restricted to melanoma because similar results were seen with breast cancer cells.

Figure 5A:
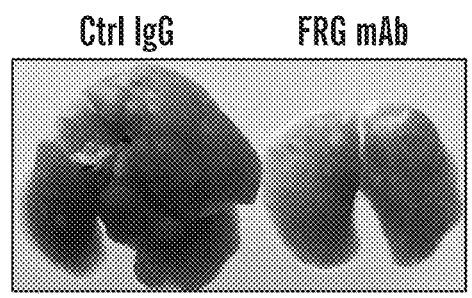
FIGS. 5A-5B demonstrate the effects of FRG on primary lung cancer.
Figure 5B:
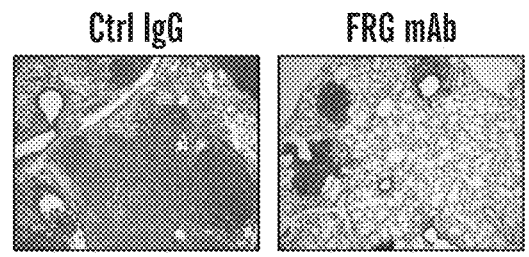
Figure 6:
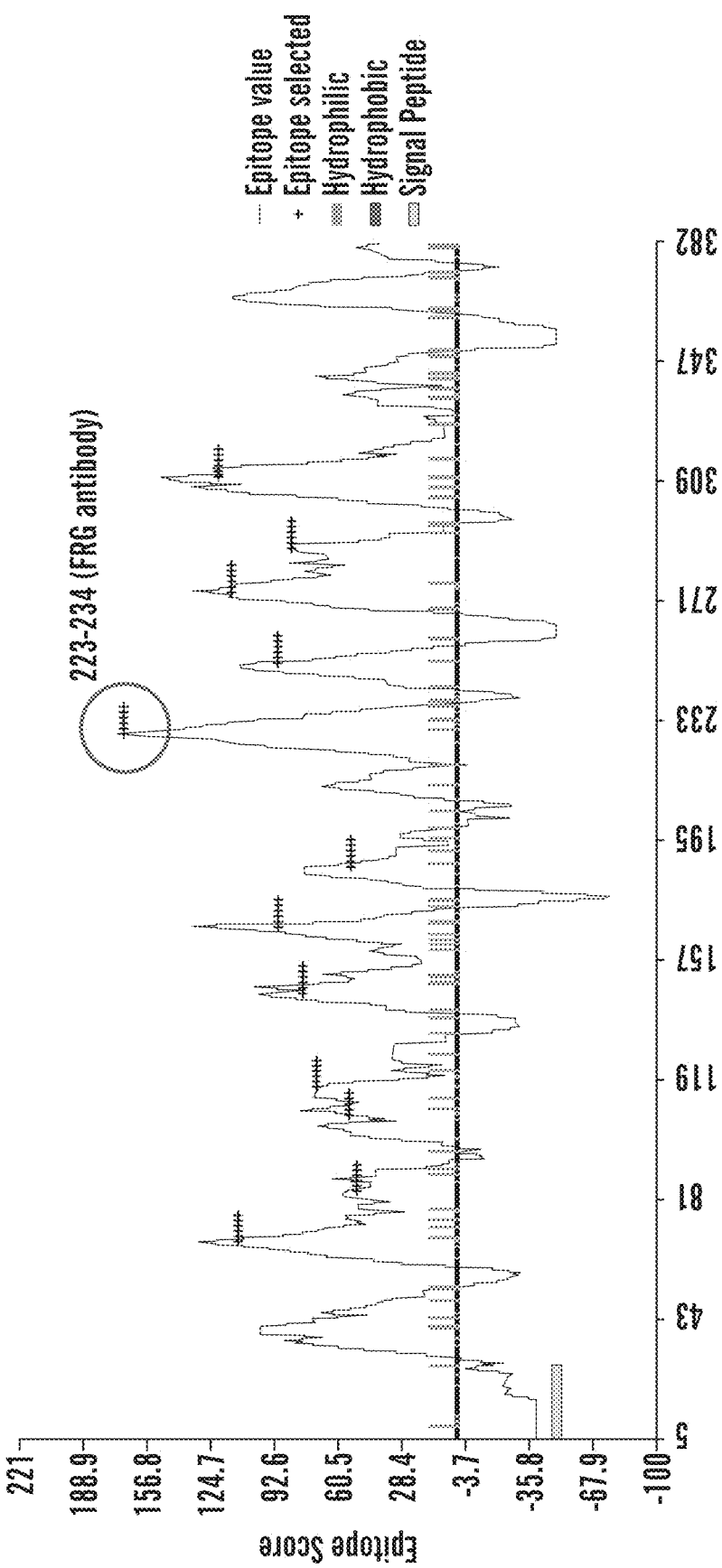
FIG. 6 depicts the location of selected epitopes including FRG in human Chi3l1.

Studies were next undertaken to determine if FRG ameliorated the generation of primary lung cancer. In these studies, primary lung cancers were induced in mice with $KRAS^{G12D}$ mutations and floxed p53 mutations (26, 27) and Chi3l1/Chil1 expression was characterized. In this model a discrete mass of tumor cells and a macrophage-rich inflammatory response can be seen 6 weeks after Adeno-Cre recombinase challenge that gradually increases over time (FIG. 5). The generation of primary lung cancers were assessed in mice that received an IgG2b control antibody or FRG at a dose of 200 μg/mouse. As can be seen in FIGS. 5A-5B, FRG was a potent inhibitor of the generation of primary lung cancers in this model.

Because of the impressive results of FRG in these in vivo models is variable regions were sequenced. The sequences are noted in Table 3.

REFERENCES CITED

1. Chupp G L, Lee C G, Jarjour N, Shim Y M, Holm C T, He S, Dziura J D, Reed J, Coyle A J, Kiener P, Cullen M, Grandsaigne M, Dombret M C, Aubier M, Pretolani M, Elias J A. A chitinase-like protein in the lung and circulation of patients with severe asthma. N Engl J Med. 2007; 357(20):2016-27. doi: 10.1056/NEJMoa073600. PubMed PMID: 18003958.
2. Konradsen J R, James A, Nordlund B, Reinius L E, Soderhall C, Melen E, Wheelock A M, Lodrup Carlsen K C, Lidegran M, Verhoek M, Boot R G, Dahlen B, Dahlen S E, Hedlin G. The chitinase-like protein YKL-40: a possible biomarker of inflammation and airway remodeling in severe pediatric asthma. J Allergy Clin Immunol. 2013; 132(2):328-35 e5. doi: 10.1016/j.jaci.2013.03.003. PubMed PMID: 23628340.
3. Gomez J L, Crisafi G M, Holm C T, Meyers D A, Hawkins G A, Bleecker E R, Jarjour N, Severe Asthma Research Program I, Cohn L, Chupp G L. Genetic variation in chitinase 3-like 1 (CHI3L1) contributes to asthma severity and airway expression of YKL-40. J Allergy Clin Immunol. 2015; 136(1):51-8 e10. doi: 10.1016/j.jaci.2014.11.027. PubMed PMID: 25592985; PMCID: PMC4494869.
4. James A J, Reinius L E, Verhoek M, Gomes A, Kupczyk M, Hammar U, Ono J, Ohta S, Izuhara K, Bel E, Kere J, Soderhall C, Dahlen B, Boot R G, Dahlen S E, Consortium B. Increased YKL-40 and Chitotriosidase in Asthma and Chronic Obstructive Pulmonary Disease. Am J Respir Crit Care Med. 2016; 193(2):131-42. doi: 10.1164/rccm.201504-07600C. PubMed PMID: 26372680.
5. Ober C, Tan Z, Sun Y, Possick J D, Pan L, Nicolae R, Radford S, Parry R R, Heinzmann A, Deichmann K A, Lester L A, Gem J E, Lemanske R F, Jr., Nicolae D L, Elias J A, Chupp G L. Effect of variation in CHI3L1 on serum YKL-40 level, risk of asthma, and lung function. N Engl J Med. 2008; 358(16):1682-91. doi: 10.1056/NEJMoa0708801. PubMed PMID: 18403759; PMCID: PMC2629486.
6. Lee C G, Hartl D, Lee G R, Koller B, Matsuura H, Da Silva C A, Sohn M H, Cohn L, Homer R J, Kozhich A A, Humbles A, Kearley J, Coyle A, Chupp G, Reed J, Flavell R A, Elias J A. Role of breast regression protein 39 (BRP-39)/chitinase 3-like-1 in Th2 and IL-13-induced tissue responses and apoptosis. J Exp Med. 2009; 206(5): 1149-66. doi: 10.1084/jem.20081271. PubMed PMID: 19414556; PMCID: PMC2715037.
7. Choi I K, Kim Y H, Kim J S, Seo J H. High serum YKL-40 is a poor prognostic marker in patients with advanced non-small cell lung cancer. Act Oncol. 2010; 49(6):861-4. PubMed PMID: 20553098.
8. Coffman F D. Chitinase 3-Like-1 (CHI3L1): a putative disease marker at the interface of proteomics and glycomics. Crit Rev Clin Lab Sci. 2008; 45(6):531-62. Epub 2008/11/13. doi: 905315713 [pii] 10.1080/10408360802334743. PubMed PMID: 19003601.
9. Iwamoto F M, Hottinger A F, Karimi S, Riedel E, Dantis J, Jandi M, Panageas K S, Lassman A B, Abrey L E, Fleisher M, Deangelis L M, Holland E C, Hormigo A. Serum YKL-40 is a marker of prognosis and disease status in high-grade gliomas. Neuro Oncol. 2011; 13(11): 1244-51. doi: 10.1093/neuonc/nor117. PubMed PMID: 21831900; PMCID: PMC3199155.
10. Johansen J S, Cintin C, Jorgensen M, Kamby C, Price P A. Serum YKL-40: a new potential marker of prognosis and location of metastases of patients with recurrent breast cancer. Eur J Cancer. 1995; 31A(9):1437-42. PubMed PMID: 7577068.
11. Johansen J S, Jensen B V, Roslind A, Nielsen D, Price P A. Serum YKL-40, a new prognostic biomarker in cancer patients? Cancer Epidemiol Biomarkers Prev. 2006; 15(2):194-202. Epub 2006/02/24. doi: 15/2/194 [pii] 10.1158/1055-9965.EPI-05-0011. PubMed PMID: 16492905.
12. Johansen J S, Schultz N A, Jensen B V. Plasma YKL-40: A potential new cancer biomarker? Future Oncol. 2009; 5(7):1065-82. PubMed PMID: 19792974.
13. Peng C, Peng J, Jiang L, You Q, Zheng J, Ning X. YKL-40 protein levels and clinical outcome of human endometrial cancer. J Int Med Res. 2010; 38(4):1448-57. PubMed PMID: 20926018.
14. Schmidt H, Johansen J S, Gehl J, Geertsen P F, Fode K, von der Maase H. Elevated serum level of YKL-40 is an independent prognostic factor for poor survival in patients with metastatic melanoma. Cancer. 2006; 106(5):1130-9. Epub 2006/02/04. doi: 10.1002/cncr.21678. PubMed PMID: 16456816.
15. Schmidt H, Johansen J S, Sjoegren P, Christensen I J, Sorensen B S, Fode K, Larsen J, von der Maase H. Serum YKL-40 predicts relapse-free and overall survival in patients with American Joint Committee on Cancer stage I and II melanoma. J Clin Oncol. 2006; 24(5):798-804. Epub 2006/01/05. doi: JCO..2005.03.7960 [pii] 10.1200/JCO.2005.03.7960. PubMed PMID: 16391295.
16. Shao R, Cao Q J, Arenas R B, Bigelow C, Bentley B, Yan W. Breast cancer expression of YKL-40 correlates with tumour grade, poor differentiation, and other cancer markers. Br J Cancer. 2011; 105(8):1203-9. doi: 10.1038/bjc.2011.347. PubMed PMID: 21934681; PMCID: PMC3208489.
17. Shao R, Hamel K, Petersen L, Cao Q J, Arenas R B, Bigelow C, Bentley B, Yan W. YKL-40, a secreted glycoprotein, promotes tumor angiogenesis. Oncogene. 2009; 28(50):4456-68. Epub 2009/09/22. doi: onc2009292 [pii] 10.1038/onc.2009.292. PubMed PMID: 19767768; PMCID: 2795793.
18. Hottinger A F, Iwamoto F M, Karimi S, Riedel E, Dantis J, Park J, Panageas K S, Lassman A B, Abrey L E, Fleisher M, Holland E C, DeAngelis L M, Hormigo A. YKL-40 and MMP-9 as serum markers for patients with primary central nervous system lymphoma. Ann Neurol. 2011; 70(1):163-9. doi: 10.1002/ana.22360. PubMed PMID: 21391238.
19. Chen C C, Pekow J, Llado V, Kanneganti M, Lau C W, Mizoguchi A, Mino-Kenudson M, Bissonnette M, Mizoguchi E. Chitinase 3-like-1 expression in colonic epithelial cells as a potentially novel marker for colitis-associated neoplasia. Am J Pathol. 2011; 179(3):1494-503. doi: 10.1016/j.ajpath.2011.05.038. PubMed PMID: 21763261; PMCID: PMC3157229.
20. Thom I, Andritzky B, Schuch G, Burkholder I, Edler L, Johansen J S, Bokemeyer C, Schumacher U, Laack E. Elevated pretreatment serum concentration of YKL-40-An independent prognostic biomarker for poor survival in patients with metastatic nonsmall cell lung cancer. Cancer. 2010; 116(17):4114-21. Epub 2010/06/22. doi: 10.1002/cncr.25196. PubMed PMID: 20564116.
21. Choi I K, Kim Y H, Kim J S, Seo J H. High serum YKL-40 is a poor prognostic marker in patients with advanced non-small cell lung cancer. Acta Oncol. 2010; 49(6):861-4. Epub 2010/06/18. doi: 10.3109/02841861003631503. PubMed PMID: 20553098.
22. Junker N, Johansen J S, Andersen C B, Kristjansen P E. Expression of YKL-40 by peritumoral macrophages in human small cell lung cancer. Lung Cancer. 2005; 48(2): 223-31. Epub 2005/04/15. doi: 10.1016/j.lungcan.2004.11.011. PubMed PMID: 15829322.
23. Johansen J S, Drivsholm L, Price P A, Christensen I J. High serum YKL-40 level in patients with small cell lung cancer is related to early death. Lung Cancer. 2004; 46(3):333-40. Epub 2004/11/16. doi: 10.1016/j.lungcan.2004.05.010. PubMed PMID: 15541818.
24. Ma B, Herzog E L, Moore M, Lee C M, Na S H, Lee C G, Elias J A. RIG-like Helicase Regulation of Chitinase 3-like 1 Axis and Pulmonary Metastasis. Sci Rep. 2016; 6:26299. doi: 10.1038/srep26299. PubMed PMID: 27198666; PMCID: PMC4873814.
25. Ma B, Herzog E L, Lee C G, Peng X, Lee C M, Chen X, Rockwell S, Koo J S, Kluger H, Herbst R S, Sznol M, Elias J A. Role of chitinase 3-like-1 and semaphorin 7a in pulmonary melanoma metastasis. Cancer Res. 2015; 75(3):487-96. doi: 10.1158/0008-5472.CAN-13-3339. PubMed PMID: 25511377; PMCID: PMC4321965.

26. Johnson L, Mercer K, Greenbaum D, Bronson R T, Crowley D, Tuveson D A, Jacks T. Somatic activation of the K-ras oncogene causes early onset lung cancer in mice. Nature. 2001; 410(6832):1111-6. Epub 2001/04/27. doi: 10.1038/35074129. PubMed PMID: 11323676.

27. Jackson E L, Olive K P, Tuveson D A, Bronson R, Crowley D, Brown M, Jacks T. The differential effects of mutant p53 alleles on advanced murine lung cancer. Cancer Res. 2005; 65(22):10280-8. Epub 2005/11/17. doi: 10.1158/0008-5472.CAN-05-2193. PubMed PMID: 16288016.

TABLE 1

Parameters considered in epitope selection algorithms.

| | |
|---|---|
| Secondary Structure | Amino Acid property |
| Loop/helix/sheet | Antigenic enhancement amino acid |
| Special region | Flexibility |
| N-terminal, C-terminal | Evolution |
| Signal peptide | Positive selection |
| Trans-membran | Discrimination |
| Disordered region | Customer requests |
| Solvent accessibility | Protein specificity |
| Blast | Region specificity |
| Query species and Mouse | Others |

TABLE 2

List of selected epitopes including FRG (ID Number 0)

| ID number | Start | End | Peptide | SEQ ID NO |
|---|---|---|---|---|
| 0 | 223 | 234 | FRGQEDASPDRF | 13 |
| 1 | 304 | 315 | RGATVHRILGQQ | 14 |
| 2 | 268 | 279 | ASSETGVGAPIS | 15 |
| 3 | 162 | 173 | IKEAQPGKKQLL | 16 |
| 4 | 62 | 73 | SNDHIDTWEWND | 17 |
| 5 | 141 | 152 | YPGRRDKQHFTT | 18 |
| 6 | 245 | 256 | LRLGAPASKLVM | 19 |
| 7 | 281 | 292 | PGIPGRFTKEAG | 20 |
| 8 | 102 | 113 | GSQRFSKIASNT | 21 |
| 9 | 181 | 192 | GKVTIDSSYDIA | 22 |
| 10 | 78 | 89 | GMLNTLKNRNPN | 23 |
| 11 | 111 | 122 | SNTQSRRTFIKS | 24 |

Location of selected epitopes including FRG in human Chi3l1 (shown below in italics; e.g., amino acids 223-234) of SEQ ID NO: 25

(SEQ ID NO: 25)
MGVKASQTGFVVLVLLQCCSAYKLVCYYTSWSQYREGDGSCFPDALDRFL

CTHIIYSFANISNDHIDTWEWNDVTLYGMLNTLKNRNPNLKTLLSVGGWN

FGSQRFSKIASNTQSRRTFIKSVPPFLRTHGFDGLDLAWLYPGRRDKQHF

TTLIKEMKAEFIKEAQPGKKQLLLSAALSAGKVTIDSSYDIAKISQHLDF

ISIMTYDFHGAWRGTTGHHSPL*FRGQEDASPDRF*SNTDYAVGYMLRLGAP

ASKLVMGIPTFGRSFTLASSETGVGAPISGPGIPGRFTKEAGTLAYYEIC

DFLRGATVHRILGQQVPYATKGNQWVGYDDQESVKSKVQYLKDRQLAGAM

VWALDLDDFQGSFCGQDLRFPLTNAIKDALAAT

TABLE 3

Sequences of variable complementarity determining regions (CDRs) of FRG antibody

| | | | SEQ ID NO: |
|---|---|---|---|
| Heavy chain (IgG2b) | CDR1 (DNA) | GYTFTNYG (GGGTATACCTTCACAAACTATGGA) | 1 7 |
| | CDR2 (DNA) | I N T Y T G E P (ATAAATACCTACACTGGAGAGCCA) | 2 8 |
| | CDR3 (DNA) | ARLGYGKFYVMDY (GCAAGATTGGGATATGGTAAATTCTATGTTATGGACTAC) | 3 9 |
| Light chain (IgG K) | CDR1 (DNA) | QSLVHSNGNTY (CAGAGCCTTGTACACAGTAATGAAACACCTAT) | 4 10 |
| | CDR2 (DNA) | K V S (AAAGTTTCC) | 5 11 |
| | CDR3 (DNA) | S Q S T H V T W T (TCTCAAAGTACACATGTTACGTGGACG) | 6 12 |

FRG Heavy chain sequence
(SEQ ID NO: 36)
QIQLVQSGPELKKPGETVKISCKASGYTFTNYGMNWVKQAPGKGLKWMGW

INTYTGEPTYADDFKGRFAFSLETSASTAYLQINNLRNEDMSTYFCARLG

YGKFYVMDYWGQGTSVTVSS

FRG Heavy chain nucleotide sequence
(SEQ ID NO: 37)
CAGATCCAGTTGGTGCAGTCTGGACCTGAGCTGAAGAAGCCTGGAGAGAC

AGTCAAGATCTCCTGCAAGGCTTCTGGGTATACCTTCACAAACTATGGAA

TGAACTGGGTGAAGCAGGCTCCAGGAAAGGGTTTAAAGTGGATGGGCTGG

ATAAATACCTACACTGGAGAGCCAACATATGCTGATGACTTCAAGGGACG

GTTTGCCTTCTCTTTGGAAACCTCTGCCAGCACTGCCTATTTGCAGATCA

ACAACCTCAGAAATGAGGACATGTCTACATATTTCTGTGCAAGATTGGGA

TATGGTAAATTCTATGTTATGGACTACTGGGGTCAGGGAACGTCAGTCAC

CGTCTCCTCA

FRG Light chain sequence
(SEQ ID NO: 38)
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQSTHVT

WTFGGGTKLEIK

FRG Heavy chain nucleotide sequence
(SEQ ID NO: 39)
GATGTTGTGATGACCCAAACTCCACTCTCCCTGCCTGTCAGTCTTGGAGA

TCAAGCCTCCATCTCTTGCAGATCTAGTCAGAGCCTTGTACACAGTAATG

GAAACACCTATTTACATTGGTACCTGCAGAAGCCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTCTCAAAGTACACATGTTACG

TGGACGTTCGGTGGAGGCACCAAGCTGGAAATCAAA

Example 3

Figure 9:
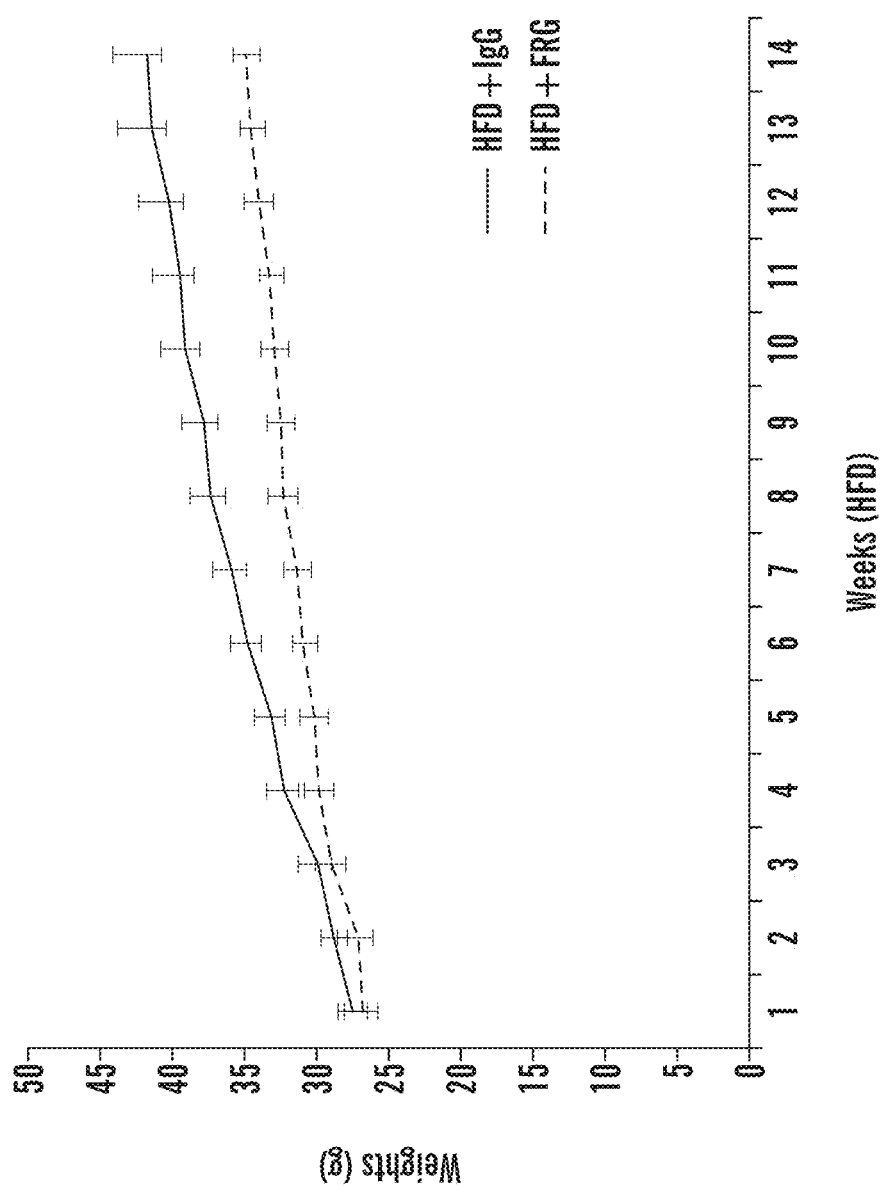
FIG. 9 depicts a graph of WT mouse whole body weight changes after 14 week HFD with & without antiChi3l1-FRG
Figure 10:
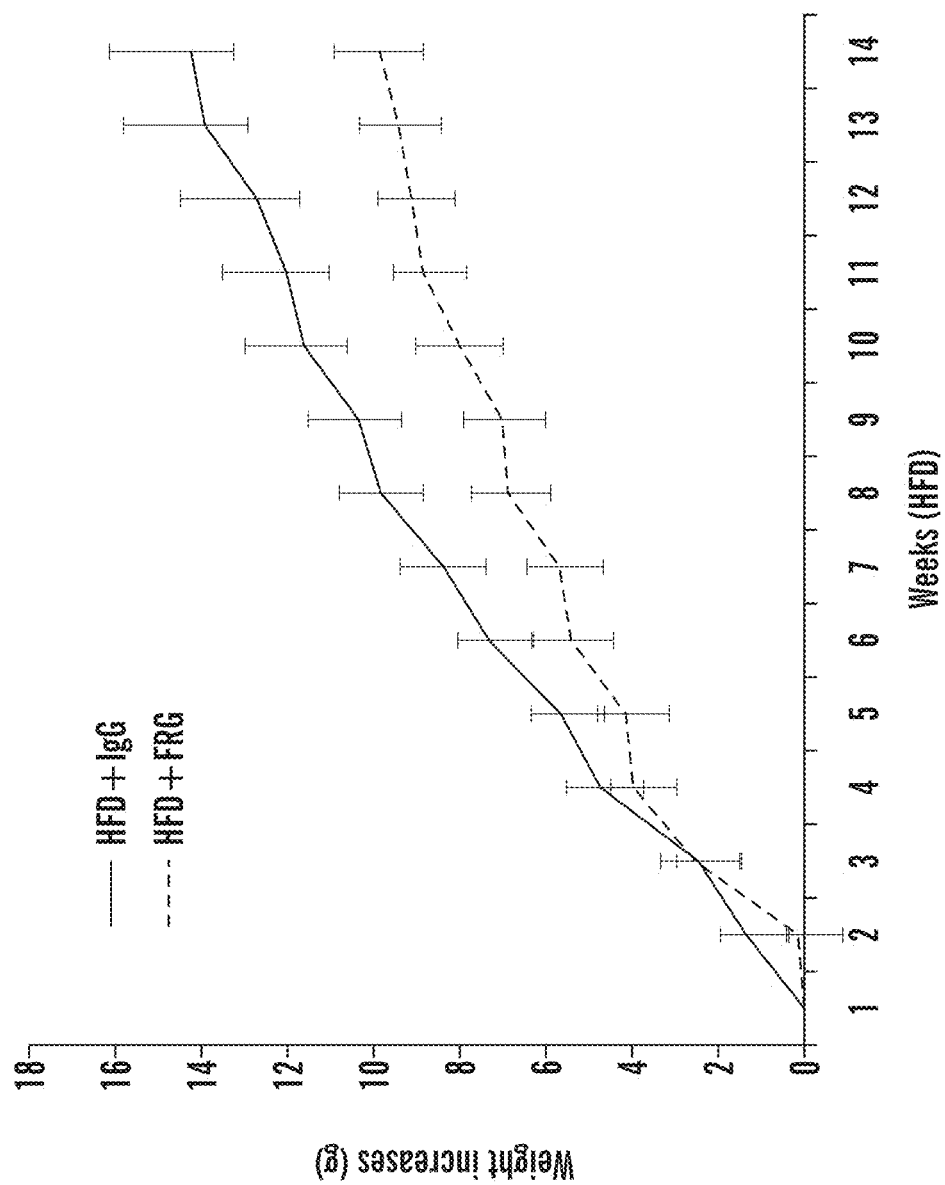
FIG. 10 depicts a graph of absolute mouse body weight increases after 14 week HFD with & without antiChi3l1-FRG

Over the course of a 14 week high fat diet (HFD), wild type mice provided anti-Chi3L1-FRG displayed less weight gain than mice provided with control IgG (FIG. 9). The weight gain is depicted in absolute weight gain in FIG. 10 and the end-point weight differences are depicted in FIG. 11.

Figure 12:
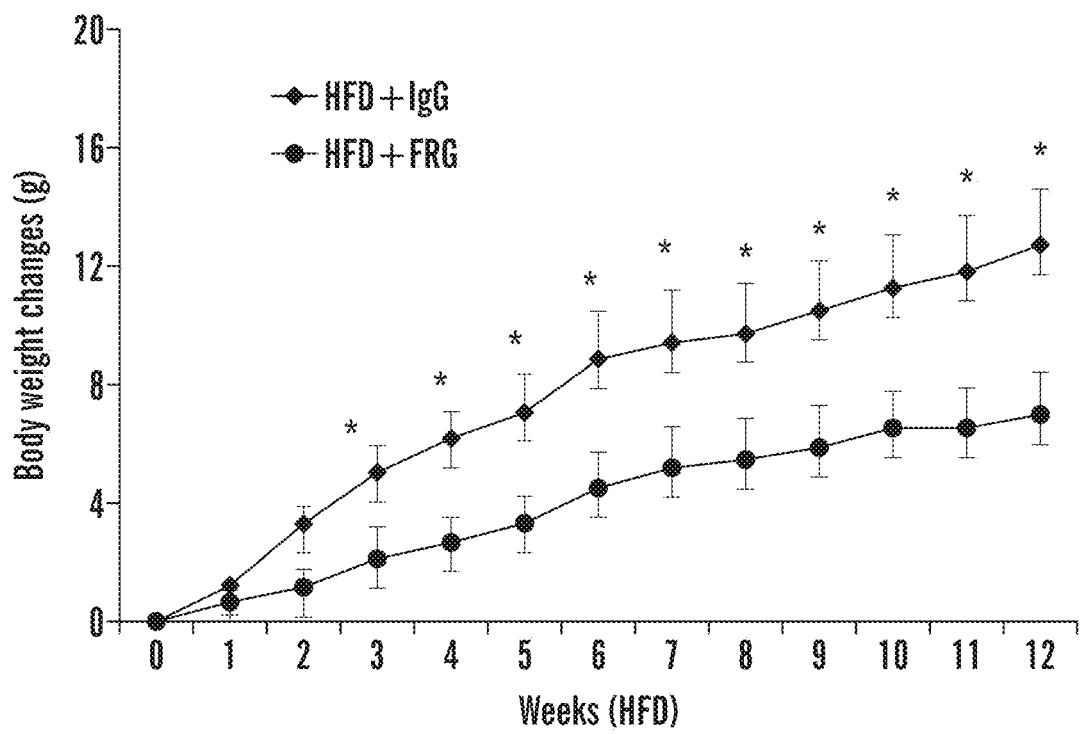
FIG. 12 depicts a graph of murine weight changes after 12 weeks on a HFD with or without FRG antibody (200 µg/twice per week).
Figure 13:
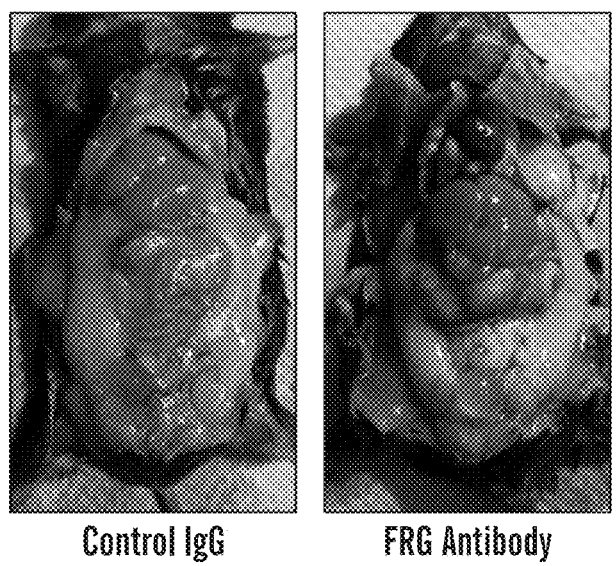
FIG. 13 depicts images of the effect of FRG antibody administration on abdominal fat accumulation after 12 weeks on a HFD with or without FRG antibody (200 µg/twice per week).
Figure 14:
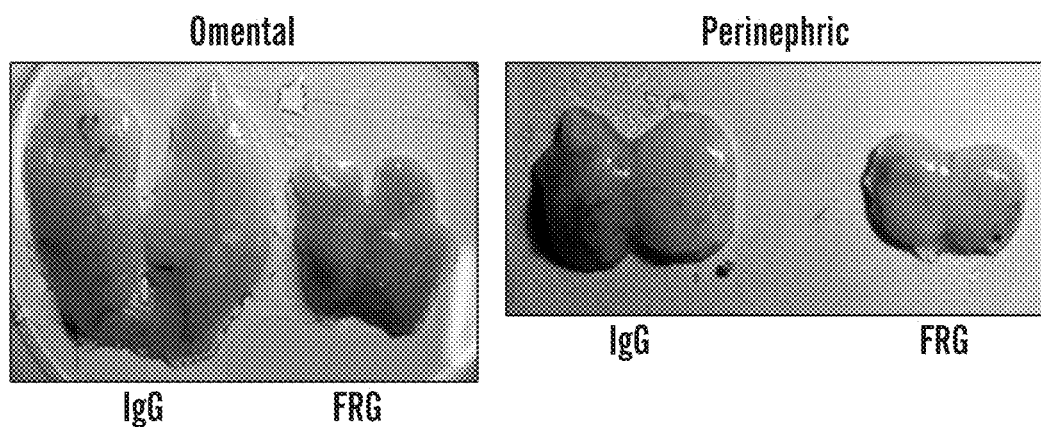
FIG. 14 depicts images of the effect of FRG antibody administration on the indicated fat pads after 12 weeks on a HFD with or without FRG antibody (200 µg/twice per week).
Figure 15:
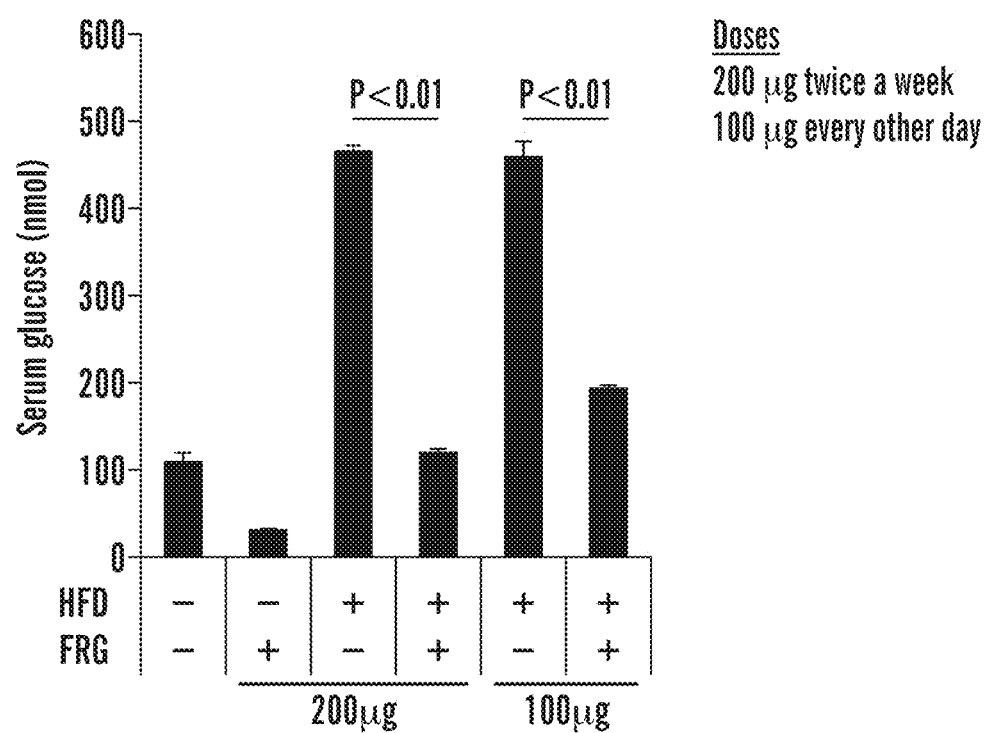
FIG. 15 depicts a graph of murine serum glucose levels after 16 weeks on a HFD with or without FRG antibody at the indicated doses.
Figure 16:
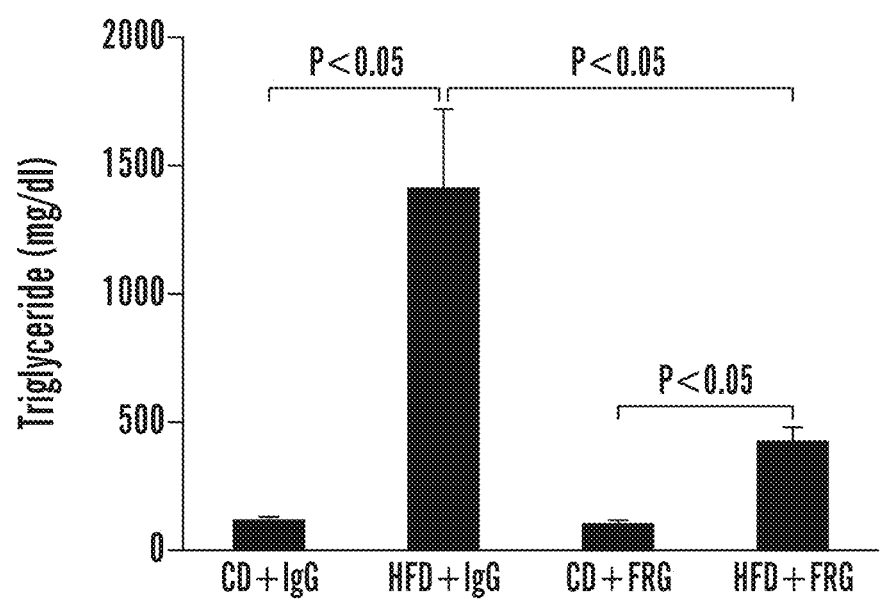
FIG. 16 depicts a graph of murine liver triglyceride levels after 16 weeks on a HFD with or without FRG antibody at the indicated doses.

Over the course of a 12 week HFD with or without FRG antibody (200 μg/twice per week), FRG administration was observed to slow weight gain (FIG. 12), reduce abdominal fat (FIG. 13) and fat pad (FIG. 14) accumulation. FRG administration also lowered serum glucose levels (FIG. 15) and liver triglycerides (FIG. 16).

What is claimed herein is:

1. A method of treating nonalcoholic steatohepatitis (NASH), nonalcoholic fatty liver disease (NFALD), or metabolic syndrome in a subject in need thereof, the method comprising administering, to the subject, a bivalent IgG antibody that specifically binds an CHI3L1 polypeptide, said bivalent IgG antibody comprising complementarity determining regions (CDRs) of:
   (a) a light chain CDR1 having the amino acid sequence of SEQ ID NO: 4;
   (b) a light chain CDR2 having the amino acid sequence of SEQ ID NO: 5;
   (c) a light chain CDR3 having the amino acid sequence of SEQ ID NO: 6;
   (d) a heavy chain CDR1 having the amino acid sequence of SEQ ID NO: 1;
   (e) a heavy chain CDR2 having the amino acid sequence of SEQ ID NO: 2; and
   (f) a heavy chain CDR3 having the amino acid sequence of SEQ ID NO: 3.

2. The method of claim 1, wherein the bivalent IgG antibody comprises a heavy chain sequence having the amino acid sequence of SEQ ID NO: 36 or a light chain sequence having the amino acid sequence of SEQ ID NO: 38.

3. The method of claim 1, wherein the bivalent IgG antibody comprises a heavy chain sequence having the amino acid sequence of SEQ ID NO: 36 and a light chain sequence having the amino acid sequence of SEQ ID NO: 38.

4. The method of claim 1, wherein bivalent IgG antibody comprises a conservative substitution relative to the heavy chain sequence having the amino acid sequence of SEQ ID NO: 36 or the light chain sequence having the amino acid sequence of SEQ ID NO: 38, wherein the conservative substitution is in a sequence not comprised by a CDR.

5. The method of claim 1, wherein the bivalent IgG antibody is selected from the group consisting of: a bivalent IgG which is fully humanized except for the CDR sequences; a monoclonal antibody, a CDR-grafted antibody, and a humanized antibody.

6. The method of claim 1, wherein the bivalent IgG antibody is administered in a pharmaceutical composition comprising the antibody and a pharmaceutically acceptable carrier.

7. The method of claim 1, wherein the subject is a subject determined to have a level of CHI3L1 that is increased compared to a reference level from healthy subjects.

8. The method of claim 7, wherein the CHI3L1 is circulating CHI3L1.

9. The method of claim 1, wherein the subject is a subject determined to have a level of CHI3LI that is increased compared to the level of CHI3LI in a prior sample obtained from the subject.

10. The method of claim 9, wherein the CHI3LI is circulating CHI3LI.

* * * * *